(12) United States Patent
Wang et al.

(10) Patent No.: US 8,507,556 B2
(45) Date of Patent: *Aug. 13, 2013

(54) FLUORESCENT PARTICLES COMPRISING NANOSCALE ZNO LAYER AND EXHIBITING CELL-SPECIFIC TOXICITY

(75) Inventors: Hua Wang, Boise, ID (US); Denise Wingett, Boise, ID (US); Kevin Feris, Boise, ID (US); Mfadhusudan R. Kongara, Boise, ID (US); Alex Punnoose, Boise, ID (US)

(73) Assignee: Boise State University, Boise, ID (US)

( * ) Notice: Subject to any disclaimer, the term of this patent is extended or adjusted under 35 U.S.C. 154(b) by 107 days.

This patent is subject to a terminal disclaimer.

(21) Appl. No.: 13/079,469

(22) Filed: Apr. 4, 2011

(65) Prior Publication Data

US 2011/0262364 A1    Oct. 27, 2011

Related U.S. Application Data

(63) Continuation-in-part of application No. 12/235,575, filed on Sep. 22, 2008, now Pat. No. 7,939,560.

(60) Provisional application No. 60/974,461, filed on Sep. 22, 2007.

(51) Int. Cl.
*A61K 31/315*    (2006.01)
*A61K 9/28*    (2006.01)

(52) U.S. Cl.
USPC ........... 514/494; 427/2.14; 977/701; 977/712

(58) Field of Classification Search
USPC ................. 514/494; 427/2.14; 977/701, 712
See application file for complete search history.

(56) References Cited

U.S. PATENT DOCUMENTS

| 6,165,440 | A | 12/2000 | Esenaliev | |
| 7,939,560 | B2 * | 5/2011 | Wang et al. | 514/494 |
| 2004/0062817 | A1 | 4/2004 | Peshoff | |
| 2004/0247861 | A1 | 12/2004 | Naasani | |
| 2006/0216759 | A1 | 9/2006 | Naasani | |
| 2007/0015226 | A1 | 1/2007 | Hirai et al. | |
| 2008/0317768 | A1 | 12/2008 | Bianchi | |
| 2009/0136580 | A1 | 5/2009 | Punnoose et al. | |
| 2009/0137666 | A1 | 5/2009 | Wang et al. | |

FOREIGN PATENT DOCUMENTS

| JP | 2007 177010 | 7/2007 |
| WO | WO 2009/039508 A2 | 3/2009 |
| WO | WO 2009/079056 A2 | 6/2009 |
| WO | WO 2009/079056 A3 | 6/2009 |

OTHER PUBLICATIONS

International Search Report and Written Opinion for PCT/US2008/077284 dated Sep. 1, 2009.
Wang et al., "Fluorescent Dye Encapsulated ZnO Particles with Cell-Specific Toxicity for Potential Use in Biomedical Applications," Journal of Material Science: Materials in Medicine (2009) 20:11-22, U.S. published online Jul. 24, 2008.
Hays et al., "Effect of Co Doping on the Structural, Optical and Magnetic Properties of ZnO Nanoparticles," Apr. 27, 2007, Journal of Physics: Condensed Matter (2007) 266203 (24pp), UK published Jun. 7, 2007.
Reddy, et al., "Selective Toxicity of Zinc Oxide Nanoparticles to Prokaryotic and Eukaryotic Systems," Applied Physics Letters, May 24, 2007, 90, 213902.
Hadadone, Zach, "Nano Cells on the Attack: BSU Researchers Find Cancer-Killing Particles," Sep. 8, 2008, Idaho Business Review.
International Preliminary Report on Patentability for PCT/US2008/077252 dated Mar. 24, 2010.
Ciardiello et al., "EGFR Antagonists in Cancer Treatment," The New England Journal of Medicine, pp. 1160-1174, Mar. 13, 2008.
Office Action for U.S. Appl. No. 12/235,415 dated Nov. 5, 2010.
Office Action for U.S. Appl. No. 12/235,415 dated Jun. 10, 2011.
U.S. Appl. No. 13/079,594, filed Apr. 4, 2011.

* cited by examiner

*Primary Examiner* — Raymond Henley, III
(74) *Attorney, Agent, or Firm* — McDermott Will & Emery LLP

(57) ABSTRACT

A core-shell nanoparticle having a core that includes a fluorophore and a first oxide of a first metal and a shell that includes a second oxide of a second metal such that the first oxide and the second oxide are different. Also disclosed are methods relating to the core-shell nanoparticle.

13 Claims, 9 Drawing Sheets

FLUORESCENT PARTICLES COMPRISING NANOSCALE ZNO LAYER AND EXHIBITING CELL-SPECIFIC TOXICITY

This application is a continuation-in-part and claims priority from U.S. Patent Application Publication Number 2009/0137666 (Ser. No. 12/235,575) filed Sep. 22, 2008, now U.S. Pat. No. 7,939,560, entitled "Fluorescent Particles Comprising Nanoscale ZnO Layer and Exhibiting Cell-Specific Toxicity," which claims priority from Provisional Application No. 60/974,461, filed Sep. 22, 2007, and entitled "Fluorescent Dye Encapsulated ZnO Particles with Cell-Specific Toxicity for Cancer Treatment and Bio-medical Applications," the entire disclosures of which are hereby incorporated herein by reference.

This research was supported in part by NSF-Idaho-EPS-CoR Program (EPS-0447689), DoE-EPSCoR grant (DE-FG02-04ER46142), NSF-CAREER award (DMR-0449639), NSF-MRI grants (MRI-052131, MRI-0619793 and MRI-0722699), and NIH awards (1 R1 5 AI06277-01A1, 1R43AR052955-01 and P20RR016454).

BACKGROUND

The present invention relates to the compositions comprising core-shell nanoparticles that preferentially associate with diseased cells, and methods relating thereto.

The ongoing worldwide nanotechnology revolution is predicted to impact several areas of biomedical research and other science and engineering applications. Nanoparticle-assisted drug delivery, cell imaging and cancer therapy are important potential biomedical applications of nanotechnology. Development of core-shell nanostructures that combine multiple functions are of great interest for future nano-biotechnology and biomedical applications. For example, core-shell nanostructures containing a chemotherapeutic drug and a fluorescent dye could be used to release the drug at sites of interest while tracking the exact location of its delivery using imaging methods employing the fluorescence of the dye molecules. Traditional tracing methods using organic dye molecules are not often successful because when a dye molecule such as fluoroescein isothiocyanate (FITC), is exposed to harsh environments, the dye molecule often suffers from freely interacting with solvent molecules, which can result in reduced performance of the dye. Encapsulation of the organic fluorescent dye in a core-shell nanostructure can add not only optical functionality, allowing the particles to be tracked and imaged easily, but can also enhance the stability and performance of the dye by protecting it from interacting negatively with surrounding solvents, e.g. photobleaching or quenching from the background medium.

Several groups have employed fluorescent core-shell nanoparticles to add functional layers that can destroy disease causing cells, including cancerous cells. Mesoporous fluorescent silica particles developed by adding molecular sieve materials such as MCM-48 were used for site-oriented delivery of chemotherapeutic drugs and cell imaging. Recently, gold coated silica nanoparticles have been used to kill tumor cells via hyperthermia treatments. However, these treatment methods employing either the conventional chemotherapeutic drugs or hyperthermia suffer from lack of significant cell specificity. These two methods can kill normal cells along with cancer cells of interest. It would be of interest to have a single platform to incorporate selective killing of diseased cells with the functionality of a fluorescent particle.

SUMMARY OF THE INVENTION

The present invention relates to the compositions comprising core-shell nanoparticles that preferentially associate with diseased cells, and methods relating thereto.

In one embodiment, the present invention provides a core-shell nanoparticle composition comprising a core that comprises a fluorophore and a first oxide of a first metal, and a first shell that comprises a second oxide of a second metal, wherein the first oxide and the second oxide are different.

In one embodiment, the present invention provides a kit comprising a set of instructions and core-shell nanoparticle comprising a core that comprises a fluorophore and a first oxide of a first metal, and a first shell that comprises a second oxide of a second metal, wherein the first oxide and the second oxide are different.

In one embodiment, the present invention provides a method comprising providing a core-shell nanoparticle comprising a core that comprises a fluorophore and a first oxide of a first metal, and a first shell that comprises a second oxide of a second metal, wherein the first oxide and the second oxide are different; providing a diseased cell and a healthy cell; contacting the diseased cell and the healthy cell with the core-shell nanoparticle; and allowing the core-shell nanoparticle to preferentially associate with the diseased cell.

The features and advantages of the present invention will be readily apparent to those skilled in the art upon a reading of the description of the preferred embodiments that follows.

BRIEF DESCRIPTION OF THE DRAWINGS

The following figures are included to illustrate certain aspects of the present invention, and should not be viewed as exclusive embodiments. The subject matter disclosed is capable of considerable modification, alteration, and equivalents in form and function, as will occur to those skilled in the art and having the benefit of this disclosure.

DETAILED DESCRIPTION

Figure 1:
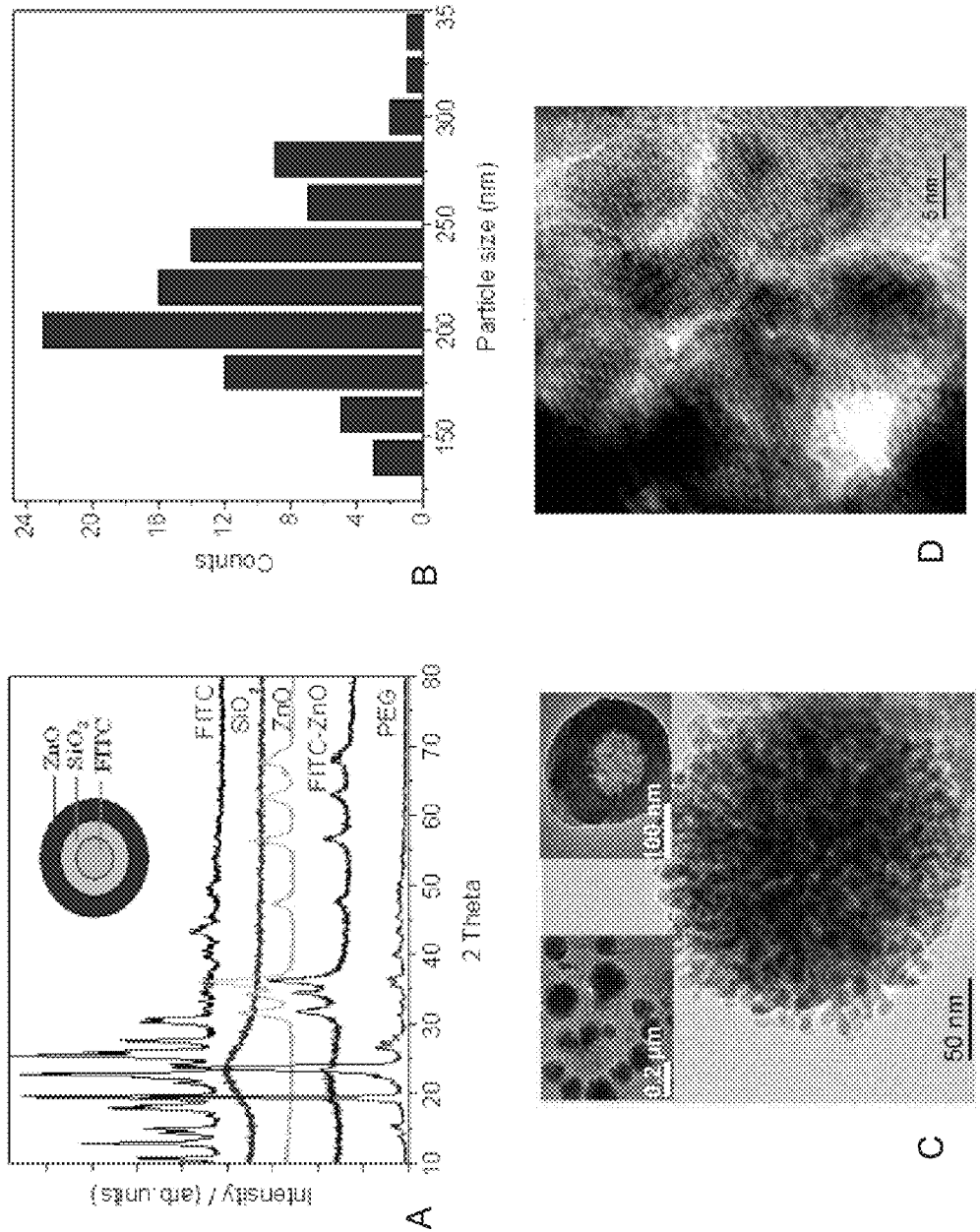
FIG. 1, A-D, is a collection of two charts and two transmission electron microscopy (TEM) images of FITC-ZnO particles.

The present invention relates to the compositions comprising core-shell nanoparticles that preferentially associate with diseased cells, and methods relating thereto.

Of the many advantages of the present invention, only a few of which are discussed or alluded to herein, the present invention provides compositions and methods of synthesizing a core-shell nanoparticle with both an metal oxide core and at least one metal oxide shell. The compositions and methods may also include a fluorophore in the metal oxide core providing at least one means of spectroscopic detection of the core-shell nanoparticle. The core-shell nanoparticles of the present invention preferentially associate with diseased cells over healthy cells without the use of a targeting ligand. The term "preferentially associate" and its derivatives as used herein refers is a relative term meaning to associating with to a higher degree wherein associating may include external contact, internalization, or adsorption. Unless otherwise specified, preferential association compares diseased to healthy. The preferential association allows for detecting, tracking, probing imaging, diagnosing, and/or treating diseased cells in vitro, in vivo, and/or ex vivo. Additionally, the core-shell nanoparticles of the present invention may have multimodal imaging characteristics that allow for combined diagnostic and/or therapeutic methods. Interestingly, the core-shell nanoparticles of the present invention also demonstrate characteristics consistent with antibacterial applications. The unique compositions and methods of use of the core-shell nanoparticles are applicable to the biological sciences, environmental sciences, and chemical sciences.

In some embodiments, the present invention provides a core-shell nanoparticle composition comprising a core that comprises a fluorophore and a first oxide of a first metal, and a first shell that comprises a second oxide of a second metal, wherein the first oxide and the second oxide are different.

In some embodiments, the present invention provides a kit comprising a set of instructions and core-shell nanoparticle comprising a core that comprises a fluorophore and a first oxide of a first metal, and a first shell that comprises a second oxide of a second metal, wherein the first oxide and the second oxide are different.

In some embodiments, the present invention provides a method comprising providing a core-shell nanoparticle comprising a core that comprises a fluorophore and a first oxide of a first metal, and a first shell that comprises a second oxide of a second metal, wherein the first oxide and the second oxide are different; providing a diseased cell and a healthy cell; contacting the diseased cell and the healthy cell with the core-shell nanoparticle; and allowing the core-shell nanoparticle to preferentially associate with the diseased cell.

It should be understood that the term "nanoparticle" or "particle," as used in this disclosure, includes all known shapes including, but not limited to, a sphere; a rod with a high to low aspect ratio; a wire; a star; a tetrapod or any other multi-legged shape; and a substantially spherical shape which may include an ovoid or a rice shape. Said shapes may be faceted.

As used herein, "core-shell" as a descriptor of a nanoparticle shall mean a core nanoparticle with at least one shell encapsulating or substantially encapsulating a core nanoparticle. Core-shell nanoparticles may have multiple shell layers, which may be described or referred to as "onion" or "onionated" core-shell nanoparticles. Unless otherwise specified, an onionated core-shell nanoparticle is equivalent to core-shell nanoparticles in the embodiments of the present invention. In some embodiments, the core and adjacent layers in a core-shell nanoparticle may be different materials, e.g. different oxides.

It should be noted that when "about" is provided at the beginning of a numerical list, "about" modifies each number of the numerical list.

In some embodiments of the present invention, a core-shell nanoparticle may comprise a metal oxide core and at least one metal oxide layer. Depending on the embodiment, the metal oxide of the core may be different from the oxide in the shell. Core-shell nanoparticles may have diameters ranging from a lower limit of about 0.5 nm, 1 nm, 5 nm, 10 nm, 25 nm, 50 nm, 100 nm, or 250 nm to an upper limit of about 500 nm, 400 nm, 300 nm, 250 nm, 100 nm, 50 nm, 25 nm, or 10 nm, wherein the diameter may range from any lower limit to any upper limit to the extent that the selected range encompasses any subset between the upper and lower limits. The core metal oxide nanoparticle may have a diameter ranging from a lower limit of about 0.5 nm, 1 nm, 5 nm, 10 nm, 25 nm, 50 nm, 100 nm, or 250 nm to an upper limit of about 500 nm, 400 nm, 300 nm, 250 nm, 100 nm, 50 nm, 25 nm, or 10 nm, wherein the diameter may range from any lower limit to any upper limit to the extent that the selected range encompasses any subset between the upper and lower limits. Depending on the embodiment, the metal oxide layer may have a thickness ranging from a lower limit of about 0.5 nm, 1 nm, 5 nm, 10 nm, 25 nm, or 50 nm to an upper limit of about 100 nm, 50 nm, 25 nm, 10 nm, or 5 nm, wherein the thickness may range from any lower limit to any upper limit to the extent that the selected range encompasses any subset between the upper and lower limits. For onionated core-shell nanoparticles, individual layers may be different thicknesses and different oxide compositions.

Suitable metal oxide core materials may be any known metal oxide nanoparticle, including, but not limited to, an oxide of magnesium, calcium, strontium, barium, scandium, titanium, vanadium, chromium, manganese, iron, cobalt, nickel, copper, zinc, molybdenum, ruthenium, palladium, silver, cadmium, tungsten, neodymium, gadolinium, erbium, aluminum, silicon, gallium, germanium, indium, tin, lead, all oxidation states thereof, and any combination thereof.

Suitable metal oxide layer materials may be any known metal oxides, including, but not limited to, an oxide of magnesium, calcium, strontium, barium, scandium, titanium, vanadium, chromium, manganese, iron, cobalt, nickel, copper, zinc, molybdenum, ruthenium, palladium, silver, cadmium, tungsten, neodymium, gadolinium, hofimium, erbium, aluminum, silicon, gallium, germanium, indium, tin, lead, all oxidation states thereof, and any combination thereof. In some embodiments, the core and subsequent shell (s) of a nanoparticle may be different oxides. One skilled in the art would understand that a metal oxide of the same metal in different oxidation states would be considered different oxides. By way of nonlimiting example, $Fe_2O_3$ compared to $Fe_3O_4$ and $\alpha\text{-}Fe_2O_3$ compared to $\gamma\text{-}Fe_2O_3$ are considered different oxides in the context of this invention.

In some embodiments, a metal oxide core may comprise a fluorophore. Suitable fluorophores may be any known fluorophore including those suitable for used in biomedical applications. Representative fluorophores include, but are not limited to, a coumarin dye including hydroxycoumarin, methoxycoumarin, aminocoumarin; a member of the ALEXA® fluor family (an sulfonated organic dye, available from Sigma-Aldrich in St. Louis, Mo.); a cyanine dye including Cy3 and Cy5; a fluorescein dye including fluorescein isothiocyanate; a rhodamine dye including tetramethyltrhodmine-5-(and 6)-isothiocyanate; a magnesium dye; a metal ligand complex; derivatives thereof; and combinations thereof.

In some embodiments, a core-shell nanoparticle may be synthesized by any known means including forced hydrolysis, precipitation, condensation, ball milling, and combinations thereof. In some embodiments, a fluorophore may be included in the core nanoparticle by being covalent functionalization to a reactant that forms the core nanoparticle, being present in the synthesis solution to be noncovalently incorporated in the core nanoparticle, being adsorbed and/or intercalated onto and/or into the core nanoparticle after synthesis, and combinations thereof.

In some embodiments, a core-shell nanoparticle may be produced by suspending a core nanoparticle in a solvent and a shell formed thereon where if the core nanoparticle is replaced with a core-shell nanoparticle an onionated core-shell nanoparticle may be produced. In some embodiments, a shell may be formed by any known means including forced hydrolysis, condensation, precipitation, and combinations thereof. In some embodiments, a one-pot synthesis may be possible by synthesizing a core nanoparticle first then in the same reaction vessel forming a shell or multiple shells on the core nanoparticle.

Suitable forced hydrolysis methods may use water to force hydrolysis of at least one transition metal salt. By way of nonlimiting example, force hydrolysis may be carried out be dissolving at least one transition metal salt in an excess of solvent, adding a volume of water, and raising the temperature of the solution. The ratio of water to transition metal salt may effect the size and/or thickness of a shell of the resultant core-shell. Suitable solvents for the forced hydrolysis may be any known solvent capable of dissolving transition metal salts and achieving a desired elevated temperature. Examples of such solvents include, but are not limited to, a glycol, an ether, an alcohol, and combinations thereof. Suitable transition metal salts may be a salt of any transition metal with any known counter anion wherein the counter anion may include, but not be limited to, a fluoride, a chloride, a bromide, an iodide, a perchlorate, a chlorate, a chlorite, a hyperchlorite, a nitride, a nitrate, a nitrite, a sulfide, a sulfate, a sulfite, an acetate, an acetylacetonate, a carbonate, a formate, a phosphate, a cyanate, a thiocyanate, derivatives thereof, and combinations thereof. Suitable temperatures for forced hydrolysis include temperatures ranging from a lower limit of about 120° C., 130° C., 140° C., 150° C., or 160° C. to an upper limit of about 200° C., 190° C., 180° C., 170° C., 160° C., or 150° C., wherein the temperature may range from any lower limit to any upper limit to the extent that the selected encompasses any subset between the upper and lower limits. In some embodiments, the solution of the transition metal salts may further include a suspended nanoparticle. Hydrolyzed transition metals may form a shell encapsulating or substantially encapsulating the provided nanoparticle to form a core-shell or an onionated nanoparticle.

Suitable precipitation methods may precipitate at least one transition metal salt by heating a solution of the transition metal salt dissolved in a solvent. Suitable temperatures for precipitation include temperatures ranging from a lower limit of about 120° C., 130° C., 140° C., 150° C., or 160° C. to an upper limit of about 200° C., 190° C., 180° C., 170° C., 160° C., or 150° C., wherein the temperature may range from any lower limit to any upper limit to the extent that the selected encompasses any subset between the upper and lower limits. Suitable solvents for the precipitation may be any known solvent capable of dissolving transition metal salts and achieving a desired elevated temperature. Examples of such solvents include, but are not limited to, a glycol, an ether, an alcohol, and combinations thereof. Suitable transition metal salts may be a salt of any transition metal with any known counter anion wherein the counter anion may include, but not be limited to, a fluoride, a chloride, a bromide, an iodide, a perchlorate, a chlorate, a chlorite, a hyperchlorite, a nitride, a nitrate, a nitrite, a sulfide, a sulfate, a sulfite, an acetate, an acetylacetonate, a carbonate, a formate, a phosphate, a cyanate, a thiocyanate, derivatives thereof, and combinations thereof. In some embodiments, the solution of the transition metal salts may further include a suspended nanoparticle. Precipitated transition metals may form a shell encapsulating or substantially encapsulating the provided nanoparticle to form a core-shell or an onionated nanoparticle.

Suitable condensation reactions may include at least one transition metal salt and heat to form a core-shell nanoparticle. Suitable temperatures for condensation include temperatures ranging from a lower limit of about 120° C., 130° C., 140° C., 150° C., or 160° C. to an upper limit of about 200° C., 190° C., 180° C., 170° C., 160° C., or 150° C., wherein the temperature may range from any lower limit to any upper limit to the extent that the selected encompasses any subset between the upper and lower limits. Suitable solvents for the condensation may be any known solvent capable of dissolving transition metal salts and achieving a desired elevated temperature. Examples of such solvents include, but are not limited to, a glycol, an ether, an alcohol, and combinations thereof. Suitable transition metal salts may be a salt of any transition metal with any known counter anion wherein the counter anion may include, but not be limited to, a fluoride, a chloride, a bromide, an iodide, a perchlorate, a chlorate, a chlorite, a hyperchlorite, a nitride, a nitrate, a nitrite, a sulfide, a sulfate, a sulfite, an acetate, an acetylacetonate, a carbonate, a formate, a phosphate, a cyanate, a thiocyanate, derivatives thereof, and combinations thereof. In some embodiments, the solution of the transition metal salts may further include a suspended nanoparticle. Condensed transition metals may form a shell encapsulating or substantially encapsulating the provided nanoparticle to form a core-shell or an onionated nanoparticle.

In some embodiments, a core-shell nanoparticle may be synthesized or modified by a method that effects the surface charge of the core-shell nanoparticle, the size of the nanoparticle core-shell, the core-shell nanoparticle composition with the addition of a dopant, the band gap or redox potential of the core-shell nanoparticle, the degree of aggregation of the core-shell nanoparticle in a solution and/or suspension, or combinations thereof. Conditions that may be adjusted during synthesis include, but are not limited to, a solvent, a reaction temperature, a reaction time, a reactant, an additional reactant for a desired dopant, addition of an additive like a surfactant, and pH. One skilled in the art would understand that by changing conditions of synthesis, core-shell nanoparticles with different characteristics including band structure, surface charge, suspendability, and degree of aggregation may be produced. Without being bound by theory or mechanism, it is believed that these parameters of a core-shell nanoparticle of the present invention may allow for influence reactive oxygen species production, a cytotoxic response to the core-shell nanoparticle, and/or a preferential association of the core-shell nanoparticle with a diseased cell.

In some embodiments, the surface charge of a core-shell nanoparticle may be changed after synthesis of the core-shell nanoparticle or controlled during synthesis of the core-shell nanoparticle. Surface charge may be measured by zeta potential. Suitable methods for changing the effective charge of a core-shell nanoparticle after synthesis of the core-shell nanoparticle include, but are not limited to, coating the core-shell nanoparticle with a polymer, surfactant, or surfmer; covalently functionalizing the core-shell nanoparticle; adjusting the pH of the core-shell nanoparticle suspension; and combinations thereof. Suitable methods for controlling the surface charge of a core-shell nanoparticle during synthesis of the core-shell nanoparticle include, but are not limited to, changing the solvent; adjusting the ratios of the two or more transition metal salts; including a polymer, surfactant, or surfmur in the synthesis solution; including a capping agent in the synthesis solution; adjusting the pH of the synthesis solution; and combinations thereof.

In some embodiments, a shell of the present invention may comprise a metal oxide and a dopant. In some embodiments, a shell of the present invention may consist essentially of a metal oxide and a dopant. In some embodiments, a shell of the present invention may consist of a metal oxide and a dopant. Suitable dopants may include, but are not limited to, transition metal ions and/or transition metal atoms that replace a metal atom/ion of the metal oxide. In some embodiments, a dopant may be distributed substantially homogeneously throughout the metal oxide, as clusters within the metal oxide, as clusters at the surface of the metal oxide, as ions or atoms at the surface of the metal oxide, and combinations thereof. Suitable dopant materials include ions or atoms of any known metal, including, but not limited to, magnesium, calcium, strontium, barium, scandium, titanium, vanadium, chromium, manganese, iron, cobalt, nickel, copper, zinc, molybdenum, ruthenium, palladium, silver, cadmium, tungsten, neodymium, gadolinium, hofimium, erbium, aluminum, silicon, gallium, germanium, indium, tin, lead, all oxidation states thereof, and any combination thereof. In some embodiments, the metal oxide and the dopant may be different. One skilled in the art would understand the same metal in different oxidation state or crystal structure would be considered different.

In some embodiments, the band gap of a core-shell nanoparticle may be controlled to provide a core-shell nanoparticle with a desired redox potential. Suitable means of controlling or changing the band gap of a core-shell nanoparticle include doping with a suitable atom/ion; controlling the core-shell nanoparticle size and shell thickness; adjusting the oxygen stochiometry of the metal oxide during synthesis of the core-shell nanoparticle; adjusting the concentration and/or compositions of a species adsorbed to the surface of a core-shell nanoparticle, e.g., $O_2$; adjusting the relative concentrations of different metal oxides that comprise the core-shell nanoparticle; and combinations thereof.

In some embodiments, suspension of core-shell nanoparticles may be aided by coating or substantially coating the core-shell nanoparticle with a polymer, surfactant, or surfmur. A polymer, surfactant, or surfmur may be any known polymer, surfactant, or surfmur including an anionic, a cationic, a nonionic, a Zwitter ion, and an ampholytic polymer, surfactant, or surfmur. In some embodiments, a monomer or partially polymerized polymer may be used to coat a core-shell nanoparticle allowing for in situ polymerization to form a coating around the core-shell nanoparticle. In some embodiments, suspension of core-shell nanoparticles may be aided by covalently functionalizing the core-shell nanoparticle.

In some embodiments, a core-shell nanoparticle may be associated with a fluorophore external to the core-shell nanoparticle. In some embodiments, the association may be covalent or noncovalent. In some embodiments, the association may be covalent attachment to a core-shell nanoparticle surface, to a core-shell nanoparticle coating, to a group covalently functionalized to the core-shell nanoparticle surface, and combinations thereof. In some embodiments, the association may be noncovalently adsorbed to the core-shell nanoparticle surface, noncovalently adsorbed within a core-shell nanoparticle surface coating and/or a plurality of covalent functional groups on the core-shell nanoparticle surface, and combinations thereof. In some embodiments, a fluorophore external to the core-shell nanoparticle and a fluorophore associated with a core core-shell nanoparticle may be the same or different.

In some embodiments, a targeting ligand may be associated with a core-shell nanoparticle, e.g., to improve selectivity. In some embodiments, the targeting ligand may be associated to the core-shell nanoparticle through direct covalent functionalization, covalent functionalization with a linker molecule, covalent functionalization to a molecule or polymer noncovalently associated with the core-shell nanoparticle, noncovalently associate with the core-shell nanoparticle, and combinations thereof. As used herein, the term "targeting ligand" may include, but is not limited to, any molecule that has specificity to a marker expressed by a cancer cell or pathogen, either extracellularly (e.g., on the cell surface or secreted by the cell) or intracellularly. In certain embodiments, the targeting ligand is specific for a tumor antigen. In some embodiments, the targeting ligand may be specific for a pathogenic antigen. Examples of a suitable targeting ligand may include, but are not limited to, antibodies and fragments thereof, haptens, polypeptides, aptemers, oligonucleotides, anti-sense RNA, Peptide Nucleic Acids, proteins, chimeric and/or fusion proteins, and the like, and any combination thereof.

In some embodiments, a core-shell nanoparticle may comprise a fluorophore in the core and a fluorophore on the surface of the nanoparticle.

In some embodiments, the environment or microenvironment of the core-shell nanoparticle may be probed by qualitatively or quantitatively analyzing fluorescence from the core-shell nanoparticle whether the fluorescence be from a fluorophore, because of the structure of the core-shell nanoparticle, or a combination of both. Suitable environmental conditions to probe may include, but are not limited to, the pH; the temperature; the pressure; the presence or absence of a small molecule, an ion, a biomolecule, a macromolecule, an element, a chemical, and/or a pathogen; the concentration of a small molecule, an ion, a biomolecule, a macromolecule, an element, a chemical, and/or a pathogen; and/or the like. In some embodiments, the core-shell nanoparticle may probe the progression of a chemical reaction or a biological process. A core-shell nanoparticle may be used to probe such conditions in gas, liquid, or solid environments.

In some embodiments, fluorescence may be observed and/or measured by eye or with the assistance of a laser, a light, a microscope, a fluorometer, a camera, and combinations thereof. One skilled in the art would recognize the available devices and methods for observing and/or measuring fluorescence.

One skilled in the art would understand that a variety of core-shell nanoparticle concentrations may be used depending on the application and method of administration. By way of nonlimiting example, suitable core-shell nanoparticle concentrations may include concentrations ranging from a lower limit of about 2 nM, 10 nM, 100 nM, 250 nM, 1 µM, 10 µM, 100 µM, 250 µM, 1 mM, 10 mM, or 100 mM, to an upper limit of about 5 M, 1 M, 250 mM, 100 mM, 10 mM, 1 mM, 250 µM, 100 µM, 10 µM, or 1 µM wherein the core-shell nanoparticle concentration may range from any lower limit to any upper limit to the extent that the selected encompasses any subset between the upper and lower limits.

In some embodiments, a core-shell nanoparticle of the present invention may be used in antibacterial applications.

As used herein, the term "bacteria" or "bacteria cell" refers to a single-celled, prokaryote microorganism. Examples of bacteria include, but are not limited to, *Acetobacter aurantius, Acinetobacter baumannii, Actinomyces israelii, Agrobacterium radiobacter, Agrobacterium tumefaciens, Azorhizobium caulinodans, Azotobacter vinelandii, Anaplasma, Bacillus, Bacteroides, Bartonella, Bordetella, Bor-*

*relia burgdorferi, Brucella, Burkholderia, Calymmatobacterium granulomatis, Campylobacter, Chlamydia, Chlamydophila, Clostridium, Corynebacterium, Ehrlichia chaffeensis, Enterobacter cloacae, Enterococcus, Escherichia coli, Francisella tularensis, Fusobacterium nucleatum, Gardnerella vaginalis, Haemophilus, Helicobacter pylori, Klebsiella pneumoniae, Lactobacillus, Legionella pneumophila, Listeria monocytogenes, Methanobacterium extroquens, Microbacterium multiforme, Micrococcus luteus, Moraxella catarrhalis, Mycobacterium, Mycoplasma, Neisseria, Pasteurella, Peptostreptococcus, Porphyromonas gingivalis, Pseudomonas aeruginosa, Rhizobium radiobacter, Rickettsia, Rochalimaea, Rothia dentocariosa, Salmonella, Shigella dysenteriae, Staphylococcus, Stenotrophomonas maltophilia, Streptococcus, Treponema, Vibrio, Wolbachia, Yersiniam*, and species thereof.

In some embodiments, bacteria cells may be exposed to a core-shell nanoparticle of the present invention. Exposing a bacteria cell to a core-shell nanoparticle may yield the core-shell nanoparticle contacting the bacteria cell; the core-shell nanoparticle becoming associated with the bacteria cell; the core-shell nanoparticle becoming internalized within the bacteria cell; the core-shell nanoparticle becoming associated with the outside of the bacteria cell; death of the bacteria cell; changes in metabolic rate of the bacteria cell; changes in reproductive rate of the bacteria cell; and combinations thereof. In some embodiments, in order to expose a bacteria cell to a core-shell nanoparticle, the core-shell nanoparticle may be incorporated into a medium including, but not limited to, a composite, a fiber, a paint, a coating, a solution, a suspension, a gel, a spray, and combinations thereof.

One skilled in the art would understand that a variety of core-shell nanoparticle concentrations may be used depending on the application and method of administration. One skilled in the art would understand that dose concentration is dependent on the administration concentration. As used herein, dose concentration refers to the concentration of core-shell nanoparticles that a bacteria, a cell, a tissue, or the like is exposed to. As used herein administration concentration refers to the concentration of core-shell nanoparticles given to a bacteria, a cell, a tissue, a patient, or the like. By way of nonlimiting example, a patient may be administered a high concentration of core-shell nanoparticles yielding a much lower dose concentration that a diseased cell in a tissue would be exposed to. Both the dose concentration and administration concentration may be varied based on a variety of factors including the patient, the illness being treated, and other factors that would make the treatment applicable to that patient and disease combination. Suitable core-shell nanoparticle administration concentrations may include concentrations ranging from a lower limit of about 2 nM, 10 nM, 100 nM, 250 nM, 1 µM, 10 µM, 100 µM, 250 µM, 1 mM, 10 mM, or 100 mM, to an upper limit of about 5M, 1 M, 250 mM, 100 mM, 10 mM, 1 mM, 250 µM, 100 µM, 10 µM, or 1 µM wherein the core-shell nanoparticle concentration may range from any lower limit to any upper limit to the extent that the selected encompasses any subset between the upper and lower limits. Suitable core-shell nanoparticle dose concentrations may include concentrations ranging from a lower limit of about 2 nM, 10 nM, 100 nM, 250 nM, 1 µM, 10 µM, 100 µM, 250 µM, 1 mM, 10 mM, or 100 mM, to an upper limit of about 250 mM, 100 mM, 10 mM, 1 mM, 250 µM, 100 µM, 10 µM, or 1 µM wherein the core-shell nanoparticle concentration may range from any lower limit to any upper limit to the extent that the selected encompasses any subset between the upper and lower limits.

In some embodiments, a core-shell nanoparticle may be used in conjunction with a diseased cell, e.g., for imaging, tracking, probing, diagnosing, and/or treating. As used herein, the term "diseased cell" refers to a cell in an abnormal condition that affects the body of an organism. Diseased cells may be associated with any known disease including, but not limited to, cancer, autoimmune disease, infectious disease, and parasitic disease. Diseased cells may be an activated T cell whose healthy counterpart would be an unactivated, non-activated, or resting T cell.

In some embodiments, a core-shell nanoparticle may be used in conjunction with a cancer cell, e.g., for imaging, tracking, probing, diagnosing, and/or treating. As used herein, the terms "cancer" or "cancer cell" refers to a cell or cells having the capacity for autonomous growth, i.e., an abnormal state or condition characterized by rapidly proliferating cell growth which generally forms a distinct mass that shows partial or total lack of structural organization and functional coordination with normal tissue. The terms are meant to encompass benign growth (i.e., nonmalignant or normeoplastic growths), hematopoietic neoplasms (e.g., lymphomas or leukemias) as well as solid neoplasms (e.g., sarcomas or carcinomas), including all types of pre-cancerous and cancerous growths, or oncogenic processes, metastatic tissues or malignantly transformed cells, tissues, or organs, irrespective of histopathologic type or stage of invasiveness. Hematopoietic neoplasms are malignant tumors affecting hematopoietic structures (structures pertaining to the formation of blood cells) and components of the immune system, including leukemias (related to leukocytes (white blood cells) and their precursors in the blood and bone marrow) arising from myeloid, lymphoid or erythroid lineages, and lymphomas (relates to lymphocytes). Solid neoplasms include sarcomas, which are malignant neoplasms that originate from connective tissues such as muscle, cartilage, blood vessels, fibrous tissue, fat or bone. Solid neoplasms also include carcinomas, which are malignant neoplasms arising from epithelial structures (including external epithelia (e.g., skin and linings of the gastrointestinal tract, lungs, and cervix), and internal epithelia that line various glands (e.g., breast, pancreas, thyroid). Examples of neoplasms that are particularly susceptible to treatment by the methods of the disclosure include leukemia, and hepatocellular cancers, sarcoma, vascular endothelial cancers, breast cancers, central nervous system cancers (e.g., astrocytoma, gliosarcoma, neuroblastoma, oligodendroglioma and glioblastoma), prostate cancers, lung and bronchus cancers, larynx cancers, esophagus cancers, colon cancers, colorectal cancers, gastro-intestinal cancers, melanomas, ovarian and endometrial cancer, renal and bladder cancer, liver cancer, endocrine cancer (e.g., thyroid), and pancreatic cancer. A cancer or tumor is treated or diagnosed according to the present methods. "Cancer" or "tumor" is intended to include any neoplastic growth in a patient, including an initial tumor and any metastases. The cancer can be of the liquid or solid tumor type. Liquid tumors include tumors of hematological origin, including, e.g., myelomas (e.g., multiple myeloma), leukemias (e.g., Waldenstrom's syndrome, chronic lymphocytic leukemia, other leukemias), and lymphomas (e.g., B-cell lymphomas, non-Hodgkins lymphoma). Solid tumors can originate in organs, and include cancers such as lung, breast, prostate, ovary, colon, kidney, and liver. As used herein, cancer cells, including tumor cells, refer to cells that divide at an abnormal (increased) rate. Cancer cells include, but are not limited to, carcinomas, such as squamous cell carcinoma, basal cell carcinoma, sweat gland carcinoma, sebaceous gland carcinoma, adenocarcinoma, papillary carcinoma, papillary adenocarcinoma, cystadenocarcinoma, medullary carcinoma, undifferentiated carcinoma, bronchogenic carcinoma, melanoma, renal cell carcinoma, hepatoma-liver cell carcinoma, bile duct carcinoma, cholangiocarcinoma, papillary carcinoma, transitional cell carcinoma, choriocarcinoma, semonoma, embryonal carcinoma, mammary carcinomas, gastrointestinal carcinoma, colonic carcinomas, bladder carcinoma, prostate carcinoma, and squamous cell carcinoma of the neck and head region; sarcomas, such as fibrosarcoma, myxosarcoma, liposarcoma, chondrosarcoma, osteogenic sarcoma, chordosarcoma, angiosarcoma, endotheliosarcoma, lymphangiosarcoma, synoviosarcoma and mesotheliosarcoma; hematologic cancers, such as myelomas, leukemias (e.g., acute myelogenous leukemia, chronic lymphocytic leukemia, granulocytic leukemia, monocytic leukemia, lymphocytic leukemia), and lymphomas (e.g., follicular lymphoma, mantle cell lymphoma, diffuse large Bcell lymphoma, malignant lymphoma, plasmocytoma, reticulum cell sarcoma, or Hodgkins disease); and tumors of the nervous system including glioma, meningoma, medulloblastoma, schwannoma or epidymoma.

In some embodiments, a core-shell nanoparticle may be used in conjunction with an autoimmune cell, e.g., for imaging, tracking, probing, diagnosing, and/or treating. As used herein, the term "autoimmune diseased cells" or "autoimmune cells," includes cells that are defective in protection from apoptosis. This defect in protection from apoptosis may be in the pathway linked to TNF-induced apoptosis, or an apoptotic pathway unrelated to TNF. Autoimmune cells of the present invention include, but are not limited to, adult splenocytes, T lymphocytes, B lymphocytes, and cells of bone marrow origin, such as defective antigen presenting cells of a mammal. Autoimmune cells may be those associated with an autoimmune disease including, but are not limited to, autoimmune disease psoriasis, rheumatoid arthritis, Crohns disease, and Lupus.

As used herein, the term "subject" and "patient" are used interchangeably herein and refer to both human and nonhuman animals and insects. The term "nonhuman animals" as used herein includes all vertebrates, e.g., mammals and non-mammals, such as nonhuman primates, sheep, dog, cat, horse, cow, chicken, amphibian, fish, reptile, and the like. The term "insects" as used herein includes all arthropods that have a chitinous exoskeleton, a three-part body (head, thorax, and abdomen), three pairs of jointed legs, compound eyes, and two antennae, e.g., bees, flies, *Drosophila* flies, beetles, and the like.

Core-shell nanoparticles of the present invention may preferentially associate with diseased cells over healthy cells with or without the assistance of a targeting ligand. Without being bound by theory or mechanism, it is believed that the preferential association and/or preferential killing of diseased cells over healthy cells stems from the characteristics of the core-shell nanoparticle of the present invention. Examples of such characteristics may include the surface charge of the core-shell nanoparticle, the size of the core-shell nanoparticle, the core-shell nanoparticle composition with the addition of a dopant, the band gap or redox potential of the core-shell nanoparticle, the degree of aggregation of the core-shell nanoparticle in a solution and/or suspension, or combinations thereof.

In some embodiments, a core-shell nanoparticle may associate preferentially with a diseased cell in vitro, in vivo, or ex vivo. In some embodiments, a core-shell nanoparticle may be associated with a diseased cell then be transferred to an in vivo and/or ex vivo environment for an application or further analysis. For example, a core-shell nanoparticle of the present invention may be introduced to a diseased cell in vitro, then said diseased cell introduced in vivo, and finally said diseased cell may be removed for ex vivo analysis. Another example may be a core-shell nanoparticle is introduced to in vivo and allowed to associate with a diseased cell then the diseased cell is analyzed ex vivo.

In some embodiments, a core-shell nanoparticle of the present invention that is associated with a cell, diseased or healthy, may allow for detecting, imaging, diagnosing, and/or treating the cell. Suitable applications and methods that exploit these possibilities include determining the location of the cell, tracking the cell location, imaging processes within the cell, tracking intracellular and extracellular processes associated with the cell, diagnosing a disease, diagnosing a diseased state, treating a diseased cell, killing a diseased cell, inducing apoptosis in a diseased cell, increasing intracellular reactive oxygen species within the cell, inducing a cytotoxic effect to the cell, and combinations thereof.

In some embodiments, a fluorescent core-shell nanoparticle may allow for the location of a nanoparticle to be determined by fluorescence thereby enabling applications including, but not limited to, core-shell nanoparticle tracking, cellular imaging, cellular tracking, ex vivo pathology, in vitro uptake, and in vivo pharmacodynamics. In some embodiments, a core-shell nanoparticle may have more than one fluorescent signal. In some embodiments, a fluorescent signal associated with a core-shell nanoparticle may interact with the environment or a chemical in the environment while a second fluorescence signal may not thereby allowing both tracking of location and measuring of concentration while monitoring a process or a condition of the environment of the core-shell nanoparticle. Such multimodal fluorescence may enable scientists or clinicians to study in vivo pharmacodynamics and pharmacokinetics in concert, to investigate intracellular processes, to diagnose diseased versus benign cells and their location in concert, to monitor the location and progress of cell death, and any other application where location and environment data may provide enhanced imaging, diagnostics, and/or therapeutics. Additional multi-modal fluorescence applications may be found in environmental science, environmental engineering, chemical engineering, and chemical physics.

In some embodiments, a core-shell nanoparticle of the present invention may be magnetic including, but not limited to, magnetic, paramagnetic, superparamagnetic, and combinations thereof. Magnetic fields may be used to control the location of the magnetic core-shell nanoparticle; to aggregate the magnetic core-shell nanoparticle; to direct the magnetic core-shell nanoparticle to a specific or general location; to detect the location of the core-shell magnetic nanoparticle; and combinations thereof. Magnetic core-shell nanoparticles associated with a cell may allow for using magnetic fields to detect the location of the cell; to move the cell; to manipulate a cell; to direct the movement of a cell; to direct the placement of a cell; to extract the cell from a given liquid media, cluster of cells, or tissue; to extract magnetic core-shell nanoparticle from the cell; and combinations thereof. In some embodiments, a core-shell nanoparticle may have magnetic properties and fluorescent properties that can be used in concert for any of the methods or any combination of methods disclosed herein.

One skilled in the art would understand that a variety of core-shell nanoparticle concentrations may be used depending on the application and method of administration. One skilled in the art would understand that dose concentration is dependent on the administration concentration. As used herein, dose concentration refers to the concentration of core-shell nanoparticles that a bacteria, a cell, a tissue, or the like is exposed to. As used herein, administration concentration refers to the concentration of core-shell nanoparticles given to a bacteria, a cell, a tissue, a patient, or the like. By way of nonlimiting example, a patient may be administered a high concentration of core-shell nanoparticles yielding a much lower dose concentration that a diseased cell in a tissue would be exposed to. Both the dose concentration and administration concentration may be varied based on a variety of factors including the patient, the illness being treated, and other factors that would make the treatment applicable to that patient and disease combination. Suitable core-shell nanoparticle administration concentrations may include concentrations ranging from a lower limit of about 2 nM, 10 nM, 100 nM, 250 nM, 1 µM, 10 µM, 100 µM, 250 µM, 1 mM, 10 mM, or 100 mM, to an upper limit of about 5M, 1 M, 250 mM, 100 mM, 10 mM, 1 mM, 250 µM, 100 µM, 10 µM, or 1 µM wherein the core-shell nanoparticle concentration may range from any lower limit to any upper limit to the extent that the selected encompasses any subset between the upper and lower limits. Suitable core-shell nanoparticle dose concentrations may include concentrations ranging from a lower limit of about 2 nM, 10 nM, 100 nM, 250 nM, 1 µM, 10 µM, 100 µM, 250 µM, 1 mM, 10 mM, or 100 mM, to an upper limit of about 250 mM, 100 mM, 10 mM, 1 mM, 250 µM, 100 µM, 10 µM, or 1 µM wherein the core-shell nanoparticle concentration may range from any lower limit to any upper limit to the extent that the selected encompasses any subset between the upper and lower limits.

A "kit" is any article of manufacture (e.g., a package or container). In some embodiments, a kit may comprise a core-shell nanoparticle of the present invention and a set of instructions. A kit may include a core-shell nanoparticle or a plurality of core-shell nanoparticles. A core-shell nanoparticle may be provided in a dry form or a wet form. Suitable dry forms include a powder, a crystal, a composite comprising a core-shell nanoparticle, and combinations thereof. Suitable wet forms include a suspension, a slurry, a solution, a paste, and combinations thereof. A kit may be promoted, distributed, or sold as a unit for performing the methods of the present invention.

A kit may be for employing a core-shell nanoparticle of the present invention without cells, in vitro, in vivo, and/or ex vivo. A core-shell nanoparticle may be administered to a patient, an animal, a bacteria, a cell, a tissue, and/or a plant. A kit may also include a means of administering the core-shell nanoparticle including, but not limited to, intravenous, intraperitoneal, intragastric, oral, intra-tumoral, topical, and combinations thereof. A kit may be used by a technician, a scientist, a student, a clinician, a nurse, and/or the like. One of ordinary skill in the art would understand additional components of a kit based on a desired imaging, analysis, tracking, diagnostic, and/or treatment application.

One skilled in the art would understand that a variety of core-shell nanoparticle concentrations may be used depending on the application and method of administration. One skilled in the art would understand that dose concentration is dependent on the administration concentration. Suitable core-shell nanoparticle administration concentrations may include concentrations ranging from a lower limit of about 2 nM, 10 nM, 100 nM, 250 nM, 1 µM, 10 µM, 100 µM, 250 µM, 1 mM, 10 mM, or 100 mM, to an upper limit of about 5M, 1 M, 250 mM, 100 mM, 10 mM, 1 mM, 250 µM, 100 µM, 10 µM, or 1 µM wherein the core-shell nanoparticle concentration may range from any lower limit to any upper limit to the extent that the selected encompasses any subset between the upper and lower limits. Suitable core-shell nanoparticle dose concentrations may include concentrations ranging from a lower limit of about 2 nM, 10 nM, 100 nM, 250 nM, 1 µM, 10 µM, 100 µM, 250 µM, 1 mM, 10 mM, or 100 mM, to an upper limit of about 250 mM, 100 mM, 10 mM, 1 mM, 250 µM, 100 µM, 10 µM, or 1 µM wherein the core-shell nanoparticle concentration may range from any lower limit to any upper limit to the extent that the selected encompasses any subset between the upper and lower limits.

In some embodiments, a core-shell nanoparticle may be in an undesired location and/or environment including, but not limited to, nature including a body of water, an aquifer, a stream, a soil, a clay, a plant, and the like; or a living organism including a human, a mammal, a vertebrate, a non-vertebrate, a bacteria, a virus, and the like. In some embodiments, a core-shell nanoparticle may produce or enhance the production of reactive oxygen species. To mitigate against and/or treat for a deleterious effect of a core-shell nanoparticle, the core-shell nanoparticle may be removed from the undesired location and/or environment. To mitigate against and/or treat for a deleterious effect of a core-shell nanoparticle, an agent may be allowed to interact with the core-shell nanoparticle or the environment effected by the core-shell nanoparticle. Suitable agents include an antioxidant, a reactive oxygen species scavenger, a base, an acid, a solvent, a polymer, a surfactant, and/or a surfiner.

To facilitate a better understanding of the present invention, the following examples of preferred embodiments are given. In no way should the following examples be read to limit, or to define, the scope of the invention.

EXAMPLES

The ability of $FITC/SiO_2$—ZnO particles for potential use in four novel biomedical applications has been demonstrated—(i) cell imaging, (ii) eukaryotic cellular uptake of particles, (iii) antibacterial treatment, and (iv) cancer treatment.

Synthesis of $FITC/SiO_2$—ZnO particles. $FITC/SiO_2$—ZnO particles were synthesized by forced hydrolysis and condensation of FITC-binding silane and silicate to obtain the $FITC-SiO_2$ core, followed by the formation of ZnO surface layer using zinc salt. In a typical synthesis, 10 mg (0.026 mmol) of FITC was dissolved in 3.0 mL ethanol by stirring for 20 min, followed by the addition of 20 µL (0.085 mmol) of vacuum-distilled (3-aminopropyl)-trimethoxysilane (APTMS). The reaction continued for 24 h under stirring in the dark. The amino group of the APTMS reacts with the isothiocyanate group of FITC to form N-1-(3-triethoxysilylpropyl)-N'-fluoresceylthiourea, and the resulting solution is referred to as FITC-APTMS. Second, 0.77 g tri-n-octylphosphine oxide (TOPO), 1.0 g polyethylene glycol (PEG), and 0.5 mL of FITC-APTMS were added to a flask containing 200 mL of diethylene glycol (DEG) solution and stirred for 10 min. Then, 0.5 mL of tetraethylorthosilicate (TEOS), 2.0 mL of water, and 1.5 mL of ammonium hydroxide (28-30%) were added into the above mixture and stirred for 1:5 h to form $FITC/SiO_2$ cores. A part of this sample was separated at this point to obtain FITC encapsulated silica particles to compare their properties with $FITC/SiO_2$ encapsulated ZnO particles. The resulting mixture was then heated to 100° C. and 2.6 g of zinc acetylacetonate, $Zn(CH_3COCHCOCH_3)_2$ was introduced. Following this, the mixture was heated to 160° C. and maintained at that temperature for 2 h. The heating was then stopped to allow the mixture to cool down to room temperature with continuous stirring for 1 h. The resulting $FITC/SiO_2$—ZnO particles were purified by centrifugation at 10,000 rpm for 8 min. The supernatant was removed and replaced with ethanol. This process was repeated for several times until no yellow fluorescence of FITC was observed in the supernatant. Subsequently, the resultant particles were dried in an oven.

Characterization of core-shell nanoparticles. The morphology, size, structure, and composition of FITC/$SiO_2$—ZnO particles were thoroughly investigated using transmission electron microscopy (TEM), X-ray diffraction (XRD), X-ray photoelectron spectroscopy (XPS), and UV-vis spectroscopy. In addition to the as-prepared samples, XPS spectra were also collected after removing 2, 5, 8, and 11 nm thick layers successively via $Ar^+$ ion sputtering using a 2 kV $Ar^+$ ion beam rastered over a 4 mm diameter sample area during 2 RPM sample rotation.

The FITC encapsulated fluorescent ZnO particles were light orange in color. FIG. 1 (panels labeled A-D) shows X-ray diffraction patterns and HRTEM images of core-shell FITC/$SiO_2$—ZnO particles. FIG. 1A illustrates X-ray diffraction spectra of FITC-ZnO particles, along with those of pure samples of PEG, FITC, ZnO and $SiO_2$ particles, wherein a schematic illustration of the FITC/$SiO_2$—ZnO particles is shown in the inset of FIG. 1A. FIG. 1B shows TEM images of FITC-ZnO particles, where the inset on the left shows a group of FITC/$SiO_2$—ZnO particles and the right inset shows a TEM image of the FITC encapsulated $SiO_2$ particles taken out during the synthesis of FITC/$SiO_2$—ZnO particles. FIG. 1C is a plot showing the size distribution of FITC/$SiO_2$—ZnO particles, and FIG. 1D is a high-resolution TEM image of the outer shell of the FITC/$SiO_2$—ZnO particles illustrating the ZnO crystallites forming the outer layer.

The inset of FIG. 1A shows the schematic representation of the particle with the expected core-shell structure. X-ray diffraction (XRD) measurements were used to investigate the material composition and chemical phases present in the FITC-ZnO particles, comparing to those of pure samples of $SiO_2$ and ZnO particles prepared under similar conditions. The XRD spectrum of the FITC/$SiO_2$—ZnO particles shown in FIG. 1A clearly has all the expected ZnO peaks in addition to the strongest peaks of polyethylene glycol (PEG) used for size control and capping agent for $SiO_2$, and for improving the hydrophilicity of FITC/$SiO_2$—ZnO particles. Only a broad peak was observed for $SiO_2$ indicating poor crystallinity. Average size of the ZnO crystallites were estimated using the Scherrer equation, $L=0.9\lambda/\beta \cos\theta$ (where 8 is the XRD peak position, $\lambda$ is the x-ray wavelength and $\beta$ is the width of the measured peak after correcting instrumental width). The estimated size of ~10 nm suggests that the outer ZnO layer was formed by attaching such nanocrystals on the surface of FITC encapsulated $SiO_2$ structures. Transmission electron microscopy (TEM) measurements were performed to investigate the particle size, shape, and size distribution of the fluorescent FITC/$SiO_2$—ZnO particles.

FIG. 1B shows spherical FITC-ZnO particles of average size ~200 nm and with a size distribution shown in FIG. 1C. The TEM data also confirms the XRD result that the surface ZnO layer is formed via accumulation of ~10 nm sized ZnO crystallites (FIG. 1D). The presence of the relatively less electron transparent ZnO nanoparticle layer on the outer surface prevented clear observation of the core-shell structure. To obtain better insight on this, a part of the sample was separated during the synthesis process before adding the ZnO precursor. This provided FITC encapsulated silica particles before attaching the ZnO nanolayer on their surface. TEM of these FITC/$SiO_2$—ZnO particles showed an electron transparent core region (brighter region) presumably containing the FITC and the spherical silica shell (darker region) as shown in FIG. 1B (top right inset).

Figure 2:
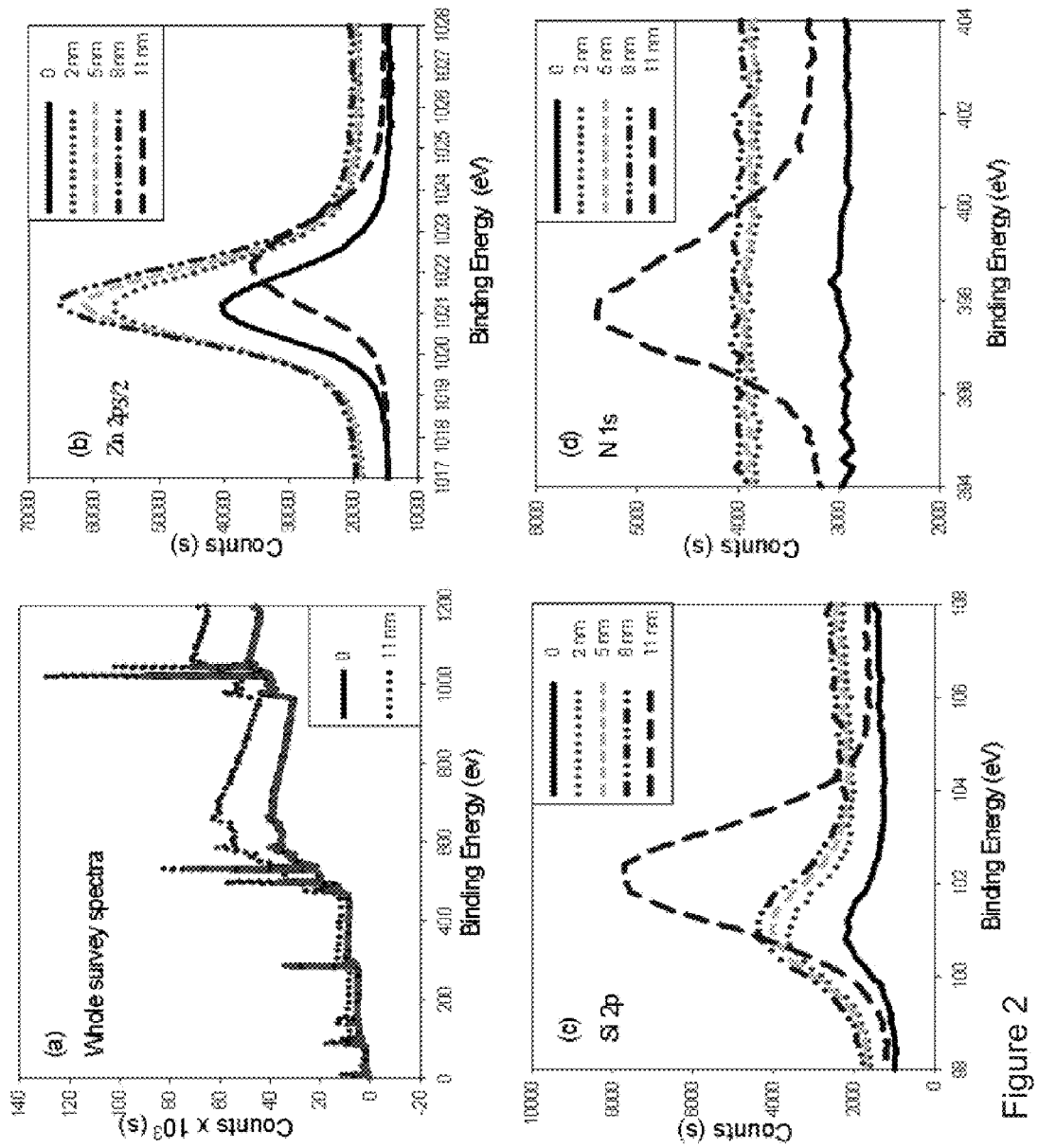
FIG. 2, A-D, is a collection of four charts about X-ray photoelectron spectroscopy (XPS) investigation of core-shell FITC-ZnO particles.

X-ray photoelectron spectroscopy (XPS) measurements were carried out to investigate the core-shell architecture of the fluorescent ZnO particles through layer-by-layer sputtering. FIG. 2 (panels labeled A-D) shows XPS investigation of core-shell FITC/$SiO_2$—ZnO particles, wherein FIG. 2A shows the XPS survey spectra of as-prepared FITC/$SiO_2$—ZnO particles and the same after removing 11 nm using Ar ion sputtering, a "whole survey spectrum." FIGS. 2B, 2C, and 2D show the high-resolution XPS spectra of the Zn $2p_{3/2}$, Si 2p, and N 1s regions, respectively, collected from as-prepared samples as well as from samples after successively removing 2, 5, 8 and 11 nm thick layers. Thus, FIGS. 2B-D show the high resolution core level spectra of the Zn $2p_{3/2}$ (FIG. 2B), Si 2p (FIG. 2C) and N 1s (FIG. 2D) regions, which are representative and distinct constituents of the ZnO, $SiO_2$, and FITC layers. FIG. 2B shows the Zn $2p_{3/2}$ peak at 1021.4 eV which is the expected binding energy range for pure ZnO. The observed increase in the peak intensity on-going from the surface of the as-prepared particles to 8 nm deep indicated more efficient packing of ZnO crystallites with increasing depth. However, further sputter removal up to 11 nm showed a drastic reduction in the peak intensity and ~1.0 eV increase in the binding energy. This is indicative of a significant change in the chemical environment, most likely a transition from the ZnO surface layer to a $SiO_2$ inner layer. Based on the observed presence of Zn in particles that underwent an 11 nm sputter removal and considering the ~12 nm analysis depth, an approximate thickness of 11-23 nm may be estimated for the ZnO surface layer. This estimate matches with the conclusion from the TEM and XRD data that the surface ZnO layer was formed by attaching ~10 nm sized ZnO crystallites on the $SiO_2$ surface. These results are further confirmed by the Si 2p peaks shown in FIG. 2C. Weaker Si 2p peaks are present even in the as-prepared samples. The nominal analysis depth of XPS is in the ~12 nm range and therefore, if the $SiO_2$ layer starts about 8-12 nm below the particle surface, a weak Si 2p signal from the outer walls of the $SiO_2$ layer is expected in the as-prepared sample as well as in samples after removing few nm thick layers. However, similar to the case of Zn $2p_{3/2}$ data shown in FIG. 2B, the Si 2p peak also shows dramatic changes when a 11 nm thick layer is removed from the sample (FIG. 2C). The Si 2p signal intensity increases significantly and shifts to higher energies by 1.4 eV. This large shift indicating a significant increase in the Si 2p binding energy can be attributed to the covalent bonding of Si ions on the inner walls of the $SiO_2$ layer with FITC molecules.

Recalling that FITC is bound covalently to the silica matrix via the (3-aminopropyl)-trimethoxysilane (APTMS) coupling agent, the results shown in FIGS. 2B and 2C indicate a layered structure of the order of ZnO—$SiO_2$-APTMS-FITC as we proceed from the surface to the core of the FITC/$SiO_2$—ZnO particle. At the boundaries of these different layers, some level of mixed interface is also expected. The N 1s peak arising from the FITC molecules shown in FIG. 2d further support the presence of such a layered architecture for the FITC/$SiO_2$—ZnO particles. Unlike the Si 2p peak, no N 1s peak (397.8 eV) was observed in the as-prepared samples suggesting that a measurable concentration of FITC molecules are not present in the surface region of the particles, at least in the ~12 nm analysis depth range of XPS. The complete absence of this peak in as-prepared samples as well as in the ones after the sputter removal of up to 8 nm, and its subsequent strong presence after removing 11 nm confirm that FITC is mostly concentrated in the core of the particles. However, since the amino group of the APTMS reacts with the isothiocyanate group of FITC and this coupled FITC-APTMS participates with tetraethylorthosilicate (TEOS) in the hydrolysis/condensation reactions, some distribution of FITC molecules in the silica shell, especially in the inner layer is a likely possibility.

The binding energy shifts of the Zn $2p_{3/2}$ peak and the Si 2p peak in the 11 nm sputter removed sample are not due to any random changes or charging effects because (i) the sample charging has been continuously compensated during the sputtering process by comparing the effect on known standards, (ii) if the binding energy shifts are due to any charging effect, it should display a gradual and systematic shift as sputtering (or charging) progresses, (iii) the peak shifts at 11 nm sputtering is associated with large changes in the intensities also indicating that the effect is related to transition between layers and the associated changes in the concentration of the elemental constituents, and (iv) the change in the XPS peaks at 11 nm sputtering coincides with the appearance of the N 1s signal from the FITC layer, again suggesting that the observed binding energy changes are associated with changes in the chemical environment/binding as data is collected progressively from different layers.

Figure 3:
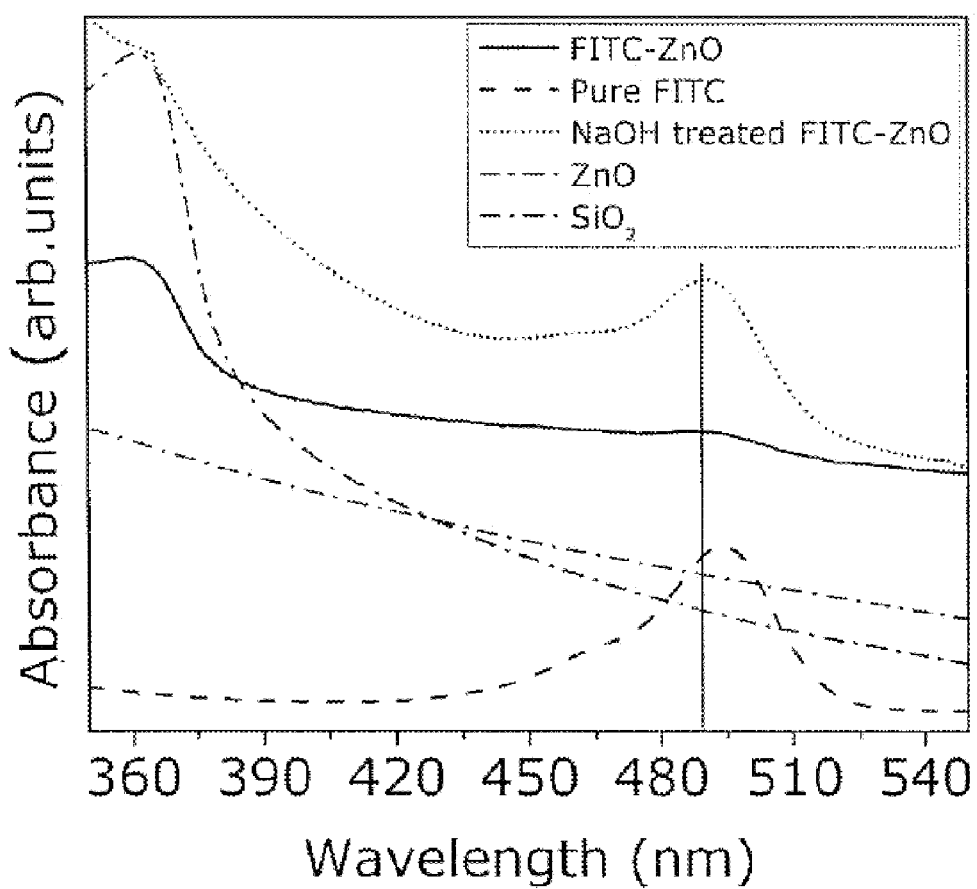
FIG. 3 is a chart about UV-vis-NIR absorption spectra of FITC-ZnO particles.

The optical properties of FITC/$SiO_2$—ZnO particles in water were studied using UV-vis-NIR spectrophotometry in the absorption mode. The spectrum of the FITC/$SiO_2$—ZnO samples was the sum of the spectral features observed in pure samples of ~10 nm ZnO particles, ~150 nm $SiO_2$, and pure FITC measured separately, as illustrated in the absorption spectra in FIG. 3. FIG. 3 discloses UV-vis-NIR absorption spectra of FITC-ZnO particles. The optical spectra of FITC/$SiO_2$—ZnO particles dispersed in water (40 mg/mL) along with pure samples of FITC ($1.2 \times 10^{-6}$ M), ZnO, and $SiO_2$, and of the FITC/$SiO_2$—ZnO particles after treatment of 1.5% NaOH to release the encapsulated FITC by dissolving the ZnO shell (NaOH treated FITC/$SiO_2$—ZnO).

The features near 362 nm in pure ZnO and FITC/$SiO_2$—ZnO are the well expected absorption edges corresponding to the band gap of ZnO. The absorption peak at 489 nm of the encapsulated FITC molecules was lower than 494 nm observed for pure FITC. This small blue shift could be the result of covalent binding of the FITC molecules on the silica shell as also evident from the XPS data discussed earlier, and/or the presence of electron rich ZnO surface layer that might electromagnetically interact with the fluorophore. The charges in ZnO and/or near the polar ZnO—$SiO_2$ interface might give rise to long-range electrostatic potential, which might extend through the silica layer to the FITC core. Another possible reason might be a direct binding of a fraction of the FITC molecules distributed in the silica shell (through the pores present in the silica layer) with ZnO nanocrystals. Additionally, UV-vis-NIR measurements were conducted for the FITC/$SiO_2$—ZnO particles after treating with 1.5% NaOH to release the encapsulated dye. The NaOH addition dissolves the ZnO layer as evident from the disappearance of the band edge (FIG. 3). From this experiment, it was found that 40 mg/mL of the FITC/$SiO_2$—ZnO particles dispersed in water might have encapsulated FITC equivalent to $1.2 \times 10^{-6}$ M of FITC, estimated by comparing the UV absorbance with that of pure dye solution.

Fluorescent emission characteristics. The fluorescence properties and stability of FITC/$SiO_2$—ZnO particles were studied using fluorescence spectroscopy and flow cytometry. For flow cytometric analysis, a 3-color Epics XL cytometer (Coulter, Miami, Fla.) was used to evaluate the photobleaching and quenching effects of FITC/$SiO_2$—ZnO particle aggregates. FITC/$SiO_2$—ZnO particles were analyzed after keeping in oxygen-rich water for varying times, and in some cases, after subjecting the samples to illumination using a mercury lamp (Model SP200 spectrum tube, with 5000V and 10 mA output) and then resuspended in oxygen-rich water prior to analysis, and a minimum of 10,000 particle aggregates monitored for changes in relative fluorescence using a 488 nm argon laser.

Fluorescence spectra of FITC/$SiO_2$—ZnO particles were measured at room temperature using a Horiba Jobin Yvon T64000 spectrometer equipped with Hamamatsu R943-02 GaAs photomultiplier. Two lines of a He—Cd laser, 441.6 and 325 run, were used for excitation. The photobleaching and quenching effects of the FITC/$SiO_2$—ZnO nanoparticles were investigated by measuring the fluorescence data at fixed time intervals after subjecting the samples to low power laser light (wavelength 441.6 nm, power density ~80 W cm-2). Similar data were also taken from pure FITC sample under identical conditions for comparison.

Figure 4:
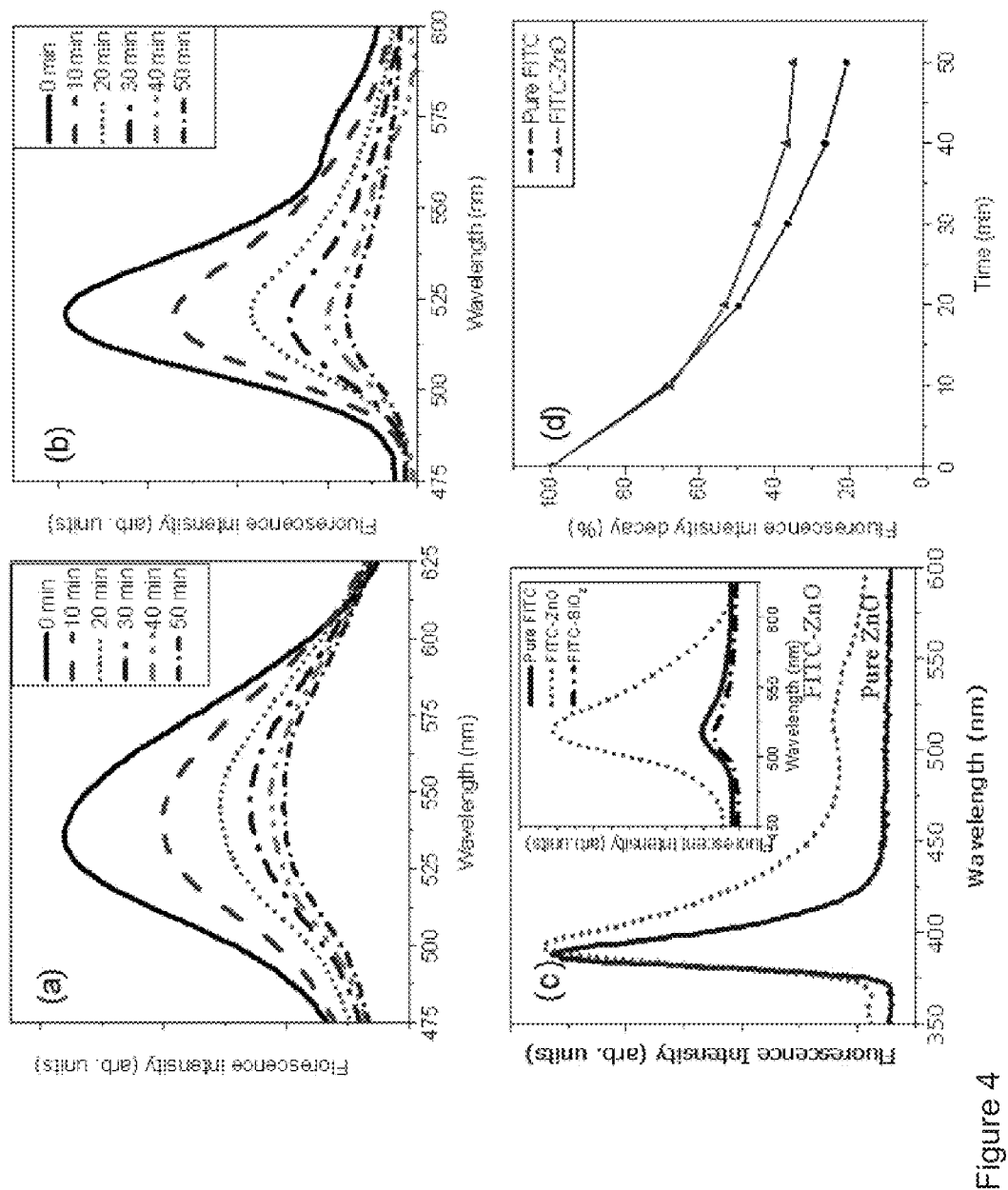
FIG. 4, A-D, is a collection of four charts about fluorescence characterization of FITC-ZnO particles.

The FITC-ZnO particles are capable of emitting strong fluorescence both in the visible and UV wavelength ranges originating from FITC and ZnO layers, respectively. FIG. 4 (panels labeled A-D) shows fluorescence characterization of FITC/$SiO_2$—ZnO particles, wherein FIG. 4A shows fluorescence emission spectra of FITC/$SiO_2$—ZnO particles and FIG. 4B shows fluorescence emission spectra of pure FITC ($1.2 \times 10^{-6}$ M), both of which were dispersed in oxygen-rich water and measured as a function of time shown. FIG. 4C shows the comparison of UV fluorescence spectra between FITC/$SiO_2$—ZnO particles and pure ZnO nanoparticles. The inset in FIG. 4C shows the FITC fluorescence from pure FITC, FITC encapsulated $SiO_2$, and FITC/$SiO_2$—ZnO; and the plot in FIG. 4D shows the relative decrease of fluorescence intensity as a function of exposure time for pure FITC sample and the FITC/$SiO_2$—ZnO particles.

Specifically, FIGS. 4A and 4B show the visible region fluorescence emission of FITC/$SiO_2$—ZnO particles and pure FITC (dispersed in water), respectively, excited by the 441.6 nm laser light. The encapsulation of FITC in the $SiO_2$ and ZnO layered shell might have caused a slight red shift and broadening, as shown in the insert of FIG. 4C. Interestingly, dye encapsulated $SiO_2$ displayed a blue shift due to the covalent binding of the dye molecules as observed by other groups also. The change of the FITC fluorescence emission when the additional ZnO layer was added is attributed to the electromagnetic interactions between the ZnO layer and the FITC molecules and/or a direct binding of some FITC molecules distributed in the silica shell as discussed earlier. Colloidal metal layers on silica nanoparticles may exhibit plasmon resonance and may significantly modify the fluorescence emission properties of the encapsulated dye molecules. The polar semiconducting ZnO surface layer might also have caused an electromagnetic interaction with FITC to exhibit the observed changes. Similar experiments employing a 325 nm UV laser produced strong UV fluorescence from ZnO layer shown in FIG. 4C. The peak emission from ZnO in FITC/$SiO_2$—ZnO particles is similar to that of ~10 nm-sized pure ZnO particles, but occurs at slightly longer wavelength (392 nm) compared to the emission from pure ZnO (387 nm). This shift is most likely due to the presence of the $SiO_2$ layer and/or the binding of FITC molecules present in the silica layer in close proximity. The UV laser and the resulting UV fluorescence from the ZnO layer also excite green fluorescence from the FITC dye, as can be seen in inset of FIG. 4C. The inner dye encapsulated in the silica particles may act as an internal standard for the ratiometric analysis. Our demonstrated ability to integrate an additional layer of UV fluorescent ZnO thus provides the core-shell particles two fluorescence sources. By choosing appropriate dye molecules and layered architectures, ZnO based core-shell particles may also form efficient platforms for ratiometric sensing applications.

Photostability. The fluorescence emission of a fluorophore may be affected by the molecular interaction between the dye and various active species in the solvent such as dissolved oxygen. To investigate the environmental and photo-stability, the FITC/SiO$_2$—ZnO particles were dispersed in oxygen-rich water and its fluorescence emission was recorded using a fluorescence spectrometer as a function of the time of laser exposure, shown in FIG. 4A. The observed changes were compared to a similar measurement conducted on micromolar concentrations of pure FITC dissolved in water, shown in FIG. 4B. A plot of integrated fluorescence intensity versus the laser light exposure time (441.6 nm line), shown in FIG. 4D, suggests that the SiO$_2$—ZnO layer offers protection against photobleaching of the FITC molecules. The decay time constants to for pure FITC and the FITC/SiO$_2$—ZnO particles estimated from fitting the data shown in FIG. 4D with exponential decay function $e^{-t/to}$ were 17 and 27 minutes respectively. Evidently, the photo-stability of FITC-SiO$_2$ particles reported by other groups is much more significant than our results. We believe that the reasons for this relatively weaker photo-stability might be the high concentration of FITC in the core of the particles and the less uniform distribution of FITC in SiO$_2$.

Figure 5:
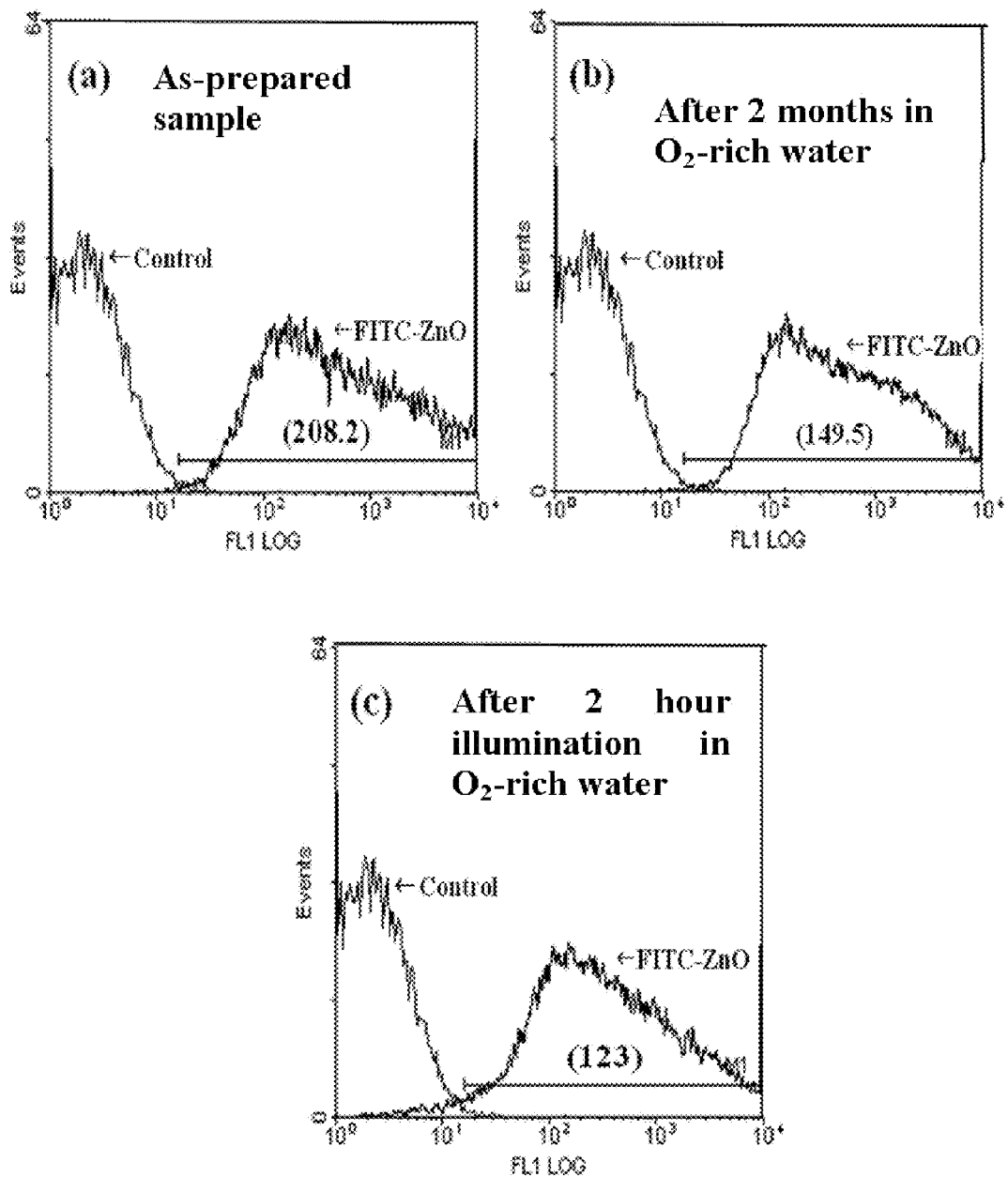
FIG. 5, A-C is a collection of three charts about flow cytometry examination of FITC-ZnO particles.

Flow cytometry is a commonly used biological/biomedical research tool and the ability of the fluorescent FITC/SiO$_2$—ZnO particles for use with this technique was carefully investigated (FIG. 5). FIG. 5 (panels labeled A-D) shows flow cytometry examination of FITC/SiO$_2$—ZnO particles. The data for FITC/SiO$_2$—ZnO particles taken (FIG. 5A) immediately after dispersing in oxygen-free water, (FIG. 5B) after keeping in oxygen-rich water for 2 months and (FIG. 5C) after exposure to a mercury lamp for 2 h. Nanoparticle aggregates were gated based on their forward scatter and side scattering light properties on a log scale with collection of 10,000 events. This identical gating region was subsequently used to determine the relative mean FL1 fluorescence signal of FITC/SiO$_2$—ZnO particles after various treatments. Unlabeled ZnO particles were used as the control sample in these experiments and numbers inside parenthesis indicate mean fluorescence intensity (MFI) of FITC/SiO$_2$—ZnO particles.

A high percentage (98%) of the freshly synthesized FITC/SiO$_2$—ZnO particle aggregates dispersed in oxygen-free water was derivatively fluorescent. As shown in FIG. 5a, a strong fluorescent signal (mean fluorescence intensity, MFI=208.2) was observed in freshly prepared FITC encapsulated particle aggregates compared to the unlabeled pure ZnO particles. Long term protection against photobleaching was also investigated using flow cytometry (FIG. 5, panels labeled A-C). For these experiments, FITC/SiO$_2$—ZnO particles were either kept in oxygen-rich water for a significantly longer period of two months (FIG. 5B) or illuminated for 2 h with a mercury lamp and then dispersed in oxygen-rich water media (FIG. 5C). Based on comparisons of the fluorescence intensities to freshly prepared FITC/SiO$_2$—ZnO particle aggregates (FIG. 5A, MFI 208.2), the fluorescence signal remained considerably stable (between 59-72%) either after storage for two months (FIG. 5B, MFI 149.5) or exposure to strong light (FIG. 5C, MFI 123) suggesting the vital role of the SiO$_2$—ZnO shell in protecting the dye from bleaching.

Utility tests for cell imaging. The feasibility of using FITC/SiO$_2$—ZnO particles for particle tracking/cell imaging in biological environments was investigated using fluorescence confocal image microscopy (FCIM). Stationary phase E. coli cells were exposed to FITC/SiO$_2$—ZnO particles and PI for 15 minutes at room temperature. FITC/SiO$_2$—ZnO and PI exposed cells were spotted on a glass slide, allowed to air dry, and viewed using a Zeiss LSM 5 Pascal confocal microscope. Additional slides were prepared with E. coli cells exposed to either the FITC/SiO$_2$—ZnO particles or propidium iodide (PI) alone to determine if there was any overlap in the fluorescence emission of the two dyes. The confocal microscope was configured to prevent detection of FITC fluorescence in the PI channel and vice versa. For cellular uptake and internalization studies, log phase Jurkat cells were adhered to poly-d-lysine treated glass bottom chamber slides (MatTek, Ashland, Mas.), treated with 0.25 mM FITC/SiO$_2$—ZnO particles for 8 hours, washed three times in PBS/3% fetal bovine serum (FBS) to remove extracellular NP, stained with a PE-conjugated antibody specific to the CD3 cell surface protein (Beckman Coulter, Miami, Fla.) as previously described using 8 µl/200 µl of cells, and washed a final time in PBS/3% FBS. For confocal analysis, control slides were prepared to verify the absence of spectral overlap between the two dyes after appropriate instrument set-up.

Figure 6:
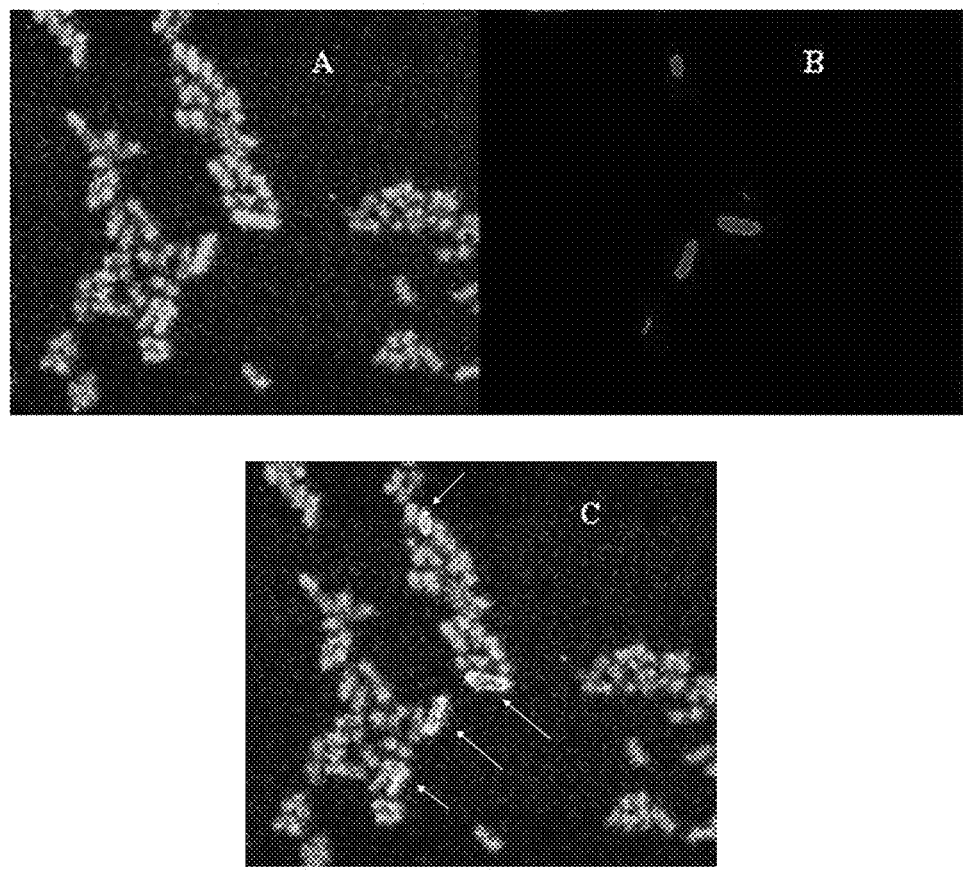
FIG. 6, A-C is three microscopic cell images with FITC-ZnO particles.

We have investigated the ability of FITC/SiO$_2$—ZnO particles (at 7.5 1.1 µg/mL) dispersed in saline medium to image E. coli using the green fluorescence of the particles (FIG. 6). E. coli cells were simultaneously stained with FITC/SiO$_2$—ZnO particles (green fluorescence), and the vital dye (propidium iodide (PI), red fluorescence). PI uptake by bacterial cells is dependent on loss of cell membrane integrity and is, therefore, frequently used to indicate the extent of death in a cell population. Bacteria co-treated with v and PI were examined by confocal microscopy to establish the ability of the FITC/SiO$_2$—ZnO particles to stain/visualize bacterial cells (FIG. 6). FIG. 6 (panels labeled A-C) shows cell imaging with FITC-ZnO particles. Confocal fluorescence microscopic images of E. coli cells simultaneously treated with FITC/SiO$_2$—ZnO particles (green fluorescence) and propidium iodide (PI, red fluorescence), showing (FIG. 6A) fluorescence signal from FITC/SiO$_2$—ZnO, (FIG. 6B) fluorescence signal from PI, and (FIG. 6C) overlay of FITC/SiO$_2$—ZnO and PI signals, yellow cells indicate dual stained cells.

Such a bivariate analysis allows for the discrimination of intact cells (FITC only) and dead/non-viable cells (FITC and PI). Visualization of the FITC/SiO$_2$—ZnO signal alone indicates that the FITC/SiO$_2$—ZnO particles were associated with the bacterial cells and emitting very bright green fluorescence (FIG. 6A). Visualization of PI signal alone indicated presence of E. coli cells with damaged and permeable cell membranes (FIG. 6B). By overlaying the FITC/SiO$_2$—ZnO and PI signals, a third image was generated where E. coli cells stained with both FITC/SiO$_2$—ZnO and PI appear yellow (FIG. 6C). The confocal images clearly demonstrate that FITC/SiO$_2$—ZnO particles have an excellent ability to image cells using common imaging techniques if they can be attached to cells of interest. This image indicates that many of the FITC/SiO$_2$—ZnO associated E. coli cells are still viable (i.e. not many yellow cells in panel C) even though the FITC/SiO$_2$—ZnO particles can be toxic to E. coli cells. This is likely due to the short incubation time (15 minutes) used to prepare the cells for imaging. The granular appearance of the E. coli cells (FIG. 6A) is due to the particulate nature of the FITC/SiO$_2$—ZnO. As discussed above the FITC-ZnO particles are ~200 nm in diameter and close to the resolution of the confocal microscope. The granular appearance of the E. coli cells is likely due to adherence of the particles to the external surface of the cells and the ability of the microscope to resolve individual fluorescent particles or groups of particles. It may be noted that the purpose of this experiment is only to demonstrate the potential of FITC/SiO$_2$—ZnO particles as a fluorescence probe and not to demonstrate selectivity in the cell-nanoparticle (FITC/SiO$_2$—ZnO) interaction.

Figure 7:
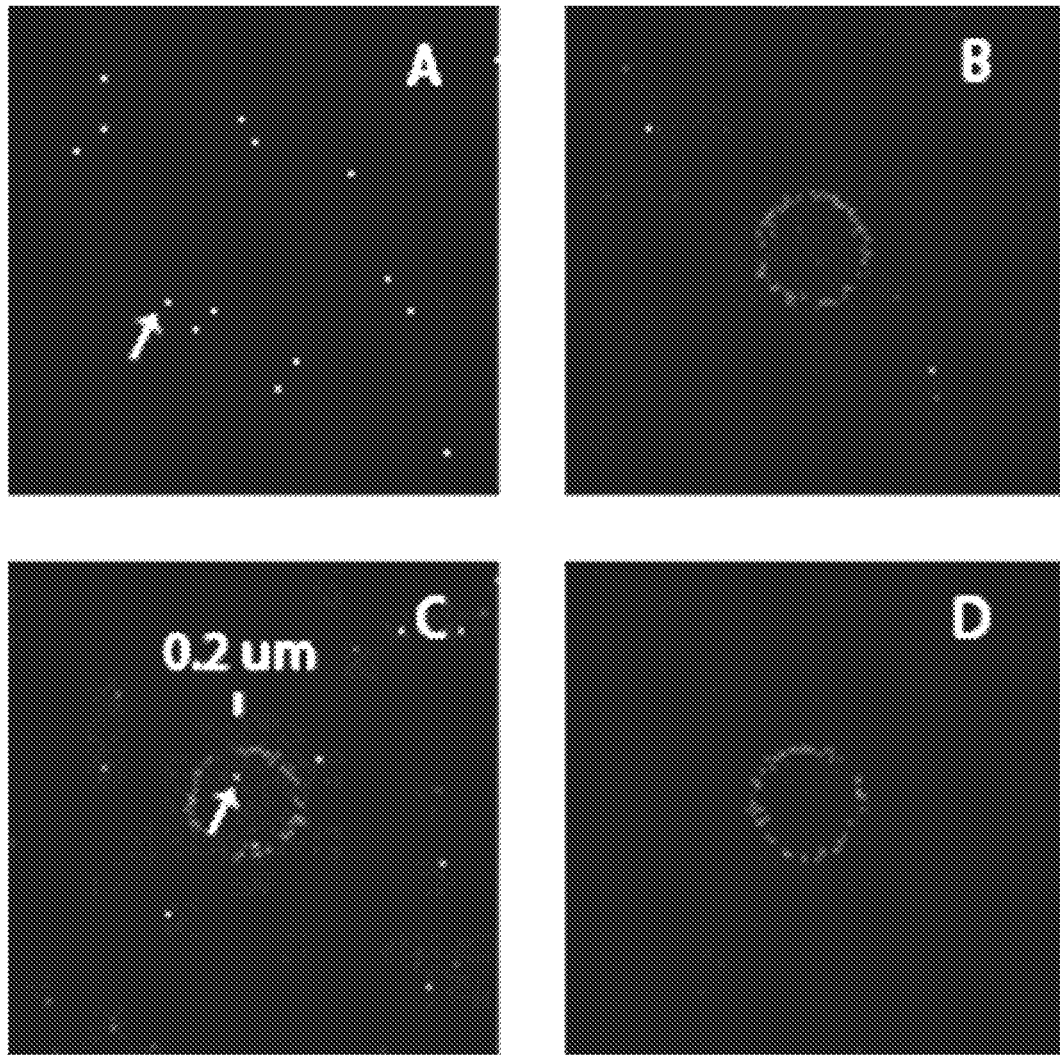
FIG. 7, A-D is four microscopic images about uptake of FITC-ZnO particles by Jurkat cancer cells.

Core-shell nanoparticle uptake and internalization studies were performed on eukaryotic Jurkat T cells as an example system. The cells were treated with FITC/SiO$_2$—ZnO particles (green fluorescence) for 8 h, and then washed extensively to remove unattached extracellular particles and reduce background staining. Cells were then stained with a PE-conjugated antibody directed against the CD3 membrane-bound protein (red fluorescence) and confocal images taken using live cells to avoid internalization artifacts resulting from cell fixation. FIG. 7 (panels labeled A-D) shows uptake of FITC/SiO$_2$—ZnO particles by Jurkat cancer cells. Confocal fluorescence microscopic images were taken of Jurkat cancer cells treated with 0.25 mM FITC/SiO$_2$—ZnO particle (green fluorescence) for 8 hours and stained with a PE-conjugated antibody specific to CD3 cell surface protein (red fluorescence) with extensive washing to remove extracellular NP. FIG. 7A depicts FITC-ZnO particles alone (after identical washing steps as samples containing cells) with an arrow indicating a typical particle of ~200 nm. FIGS. 7B-D show consecutive cell images/slices of a single cell. In FIG. 7C, an internalized particle of expected 200 nm size is indicated by an arrow and orthogonal viewing was used to confirm particle intracellular localization.

FIG. 7 shows consecutive three-dimensional slices through a single Jurkat T cell (panels B-D) demonstrating the internalization of a green fluorescent FITC-ZnO particle with intracellular localization being confirmed by viewing along orthogonal directions (not shown). Individual confocal image slices were taken at intervals of 200 nm thickness (comparable in size to the NP), thus only one internalized particle is shown in the presented focal plane. However, at least six internalized NP were observed in this particular cell with additional internalizations likely but too proximate to the plasma membrane to accurately resolve. The presence of such internalized FITC-ZnO particles was confirmed in multiple cells present on the culture slide. The image in panel A reflects NP background staining and was obtained by treating a chamberslide with an identical concentration of NP and sample washing regime as for cell cultures. It is important to note that the goal of this particular study was to specifically show NP uptake and intracellular localization in intact T cells following a short NP exposure prior to extensive cytotoxicity being manifested in contrast to simply observing FITC/SiO$_2$—ZnO association with cells (either extracellular or intracellular) as performed for FIG. 6.

Antibacterial capacity. We have recently shown that ZnO nanoparticles can selectively kill certain bacteria including *E. coli* and *S. aureus*. FITC/SiO$_2$—ZnO particles were resuspended in sterile 0.9% NaCl aqueous solution, then sonicated for 15 minutes in a bath sonicator and continuously agitated by pipetting prior to dispensing to LB media for toxicity testing. For inhibitory threshold determination resuspended FITC/SiO$_2$—ZnO particles were added to Luria-Bertani (LB) agar to different final concentrations (0-1250 µg/mL), as described in our earlier work. Time dependent toxicity tests were performed as follows. Equal densities of overnight *E. coli* cultures (based on OD$_{600\,nm}$ values) were used to inoculate LB broth with and without FITC/SiO$_2$—ZnO particles. Broth cultures were incubated with shaking as above, sampled repeatedly, and viable cell densities measured via CFU enumeration by plating on particle free LB media.

Here we demonstrate a similar ability of FITC/SiO$_2$—ZnO particles to inhibit the growth of these two organisms. FIG. 8A shows the number of bacterial colony forming units (CFU) produced by *E. coli* and *S. aureus*, after being grown in the presence of FITC/SiO$_2$—ZnO particles overnight. FITC/SiO$_2$—ZnO particles prevented growth of *E. coli* at concentrations $\geq$500 µg/mL, whereas concentrations $\geq$250 µg/mL prevented growth of *S. aureus*. The relative difference in toxicity of FITC/SiO$_2$—ZnO particles to *E. coli* and *S. aureus* is similar to that previously reported by our group for ZnO nanoparticles, 11 thus suggesting that the FITC/SiO$_2$—ZnO particles retain bacterial toxicity similar to the pure ZnO nanoparticles. Additional, time dependent exposures were conducted by enumerating CFU of *E. coli* after 0, 6, 12, 24 and 48 hours of FITC/SiO$_2$—ZnO particle exposure (FIG. 8B). Exposure to FITC/SiO$_2$—ZnO particles resulted in cell death at concentrations of 800 µg/mL with the number of viable bacterial cells reduced to below 99.9% of the initial CFU/mL within 12 hours. Viable cells were completely absent after 48 hours of treatment.

Figure 8:
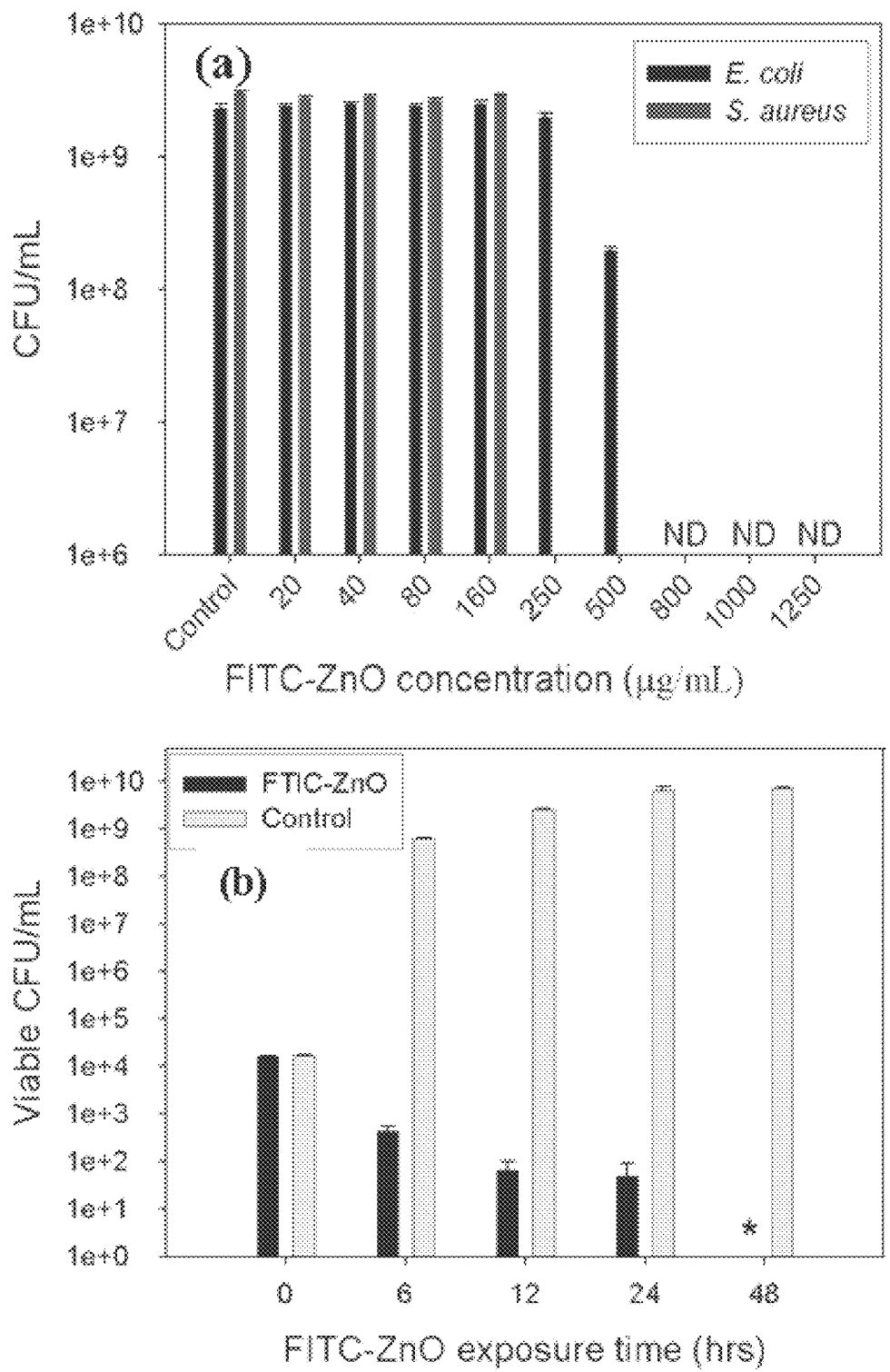
FIG. 8, (a)-(b) is a collection of two charts about concentration and time-dependent cytotoxicity of FITC-ZnO particles for bacterial systems.

FIG. 8 shows concentration and time dependent cytotoxicity of FITC/SiO$_2$—ZnO particles for bacterial systems. In FIG. 8A, *E. coli* and *S. aureus* cells were plated on LB media containing varying concentrations of FITC/SiO$_2$—ZnO particles and incubated at 37° C. for 24 h. Bars represent means±standard errors (n=3), ND indicates concentrations at which no bacterial colonies were detected after 48 h of incubation. In FIG. 8B, there is shown effect of FITC/SiO$_2$—ZnO exposure time on the viability and growth of *E. coli*. (Plot presents mean CFU/mL (±standard error, n=3) of *E. coli* exposed to 800 µg/L FITC/SiO$_2$—ZnO particles for 0, 6, 12, 24, and 48 hours, and * in the figure indicates measured ZnO concentrations at which no CFU counts of *E. coli* were observed.)

Selectivity toward cancer. To determine whether FITC encapsulated particles with nanoscale ZnO outer surface can retain the ability of differentially killing cancer cells, new experiments were conducted. Toxicity of the FITC/SiO$_2$—ZnO particles toward human T lymphocytes and Jurkat cancer cells was determined as follows. First, peripheral blood mononuclear cells (PBMC) were obtained by Ficoll-Hypaque (Histopaque-1077, Sigma, St. Louis, Mo.) gradient centrifugation using heparinized blood samples from healthy volunteers. This cell mixture was washed 3 times with Hank's buffer (Sigma), and incubated at 1.0×10$^6$ cells/mL in RPMI-1640 (Sigma) containing 10% fetal bovine serum. CD4$^+$ T cells were subsequently isolated using negative immunomagnetic selection per manufacturer's instructions using a cocktail of antibodies against CD45RO, CD8, CD19, CD14, CD16, CD56, CD8, and glycophorin A (StemCell Technologies, Vancouver, B.C.) with collection of unlabeled T cells (typically >96% CD4$^+$ and >93% viable as assessed by flow cytometry). Purified CD4$^+$ T cells, or the Jurkat T cell line (ATCC, Rockville, Md.) were cultured in RPMI/10% FCS at 5×10$^5$ cells/mL in 96-well microliter plates and treated with various concentrations of FITC/SiO$_2$—ZnO particles resuspended in PBS. For the delivery of FITC/SiO$_2$—ZnO particles to cell cultures, a stock solution was made and sonicated for 10 minutes. Then immediately prior to dispensing into each individual cell culture well, particles were vortexed and immediately dispensed. This process was repeated for each culture well, to reduce differential particle delivery due to sedimentation. After 24 h of culture, cells were stained with propidium iodide (PI; BD Biosciences, San Jose, Calif.) to monitor loss of membrane integrity as previously reported and 10 µL, of fluorescently labeled microspheres (Molecular Probes, Eugene, Oreg.) added to each sample to allow for the absolute determination of cell numbers. Flow cytometry was used to analyze a minimum of 10,000 T cells per sample to determine changes in PI staining and quantification of cell death.

Figure 9:
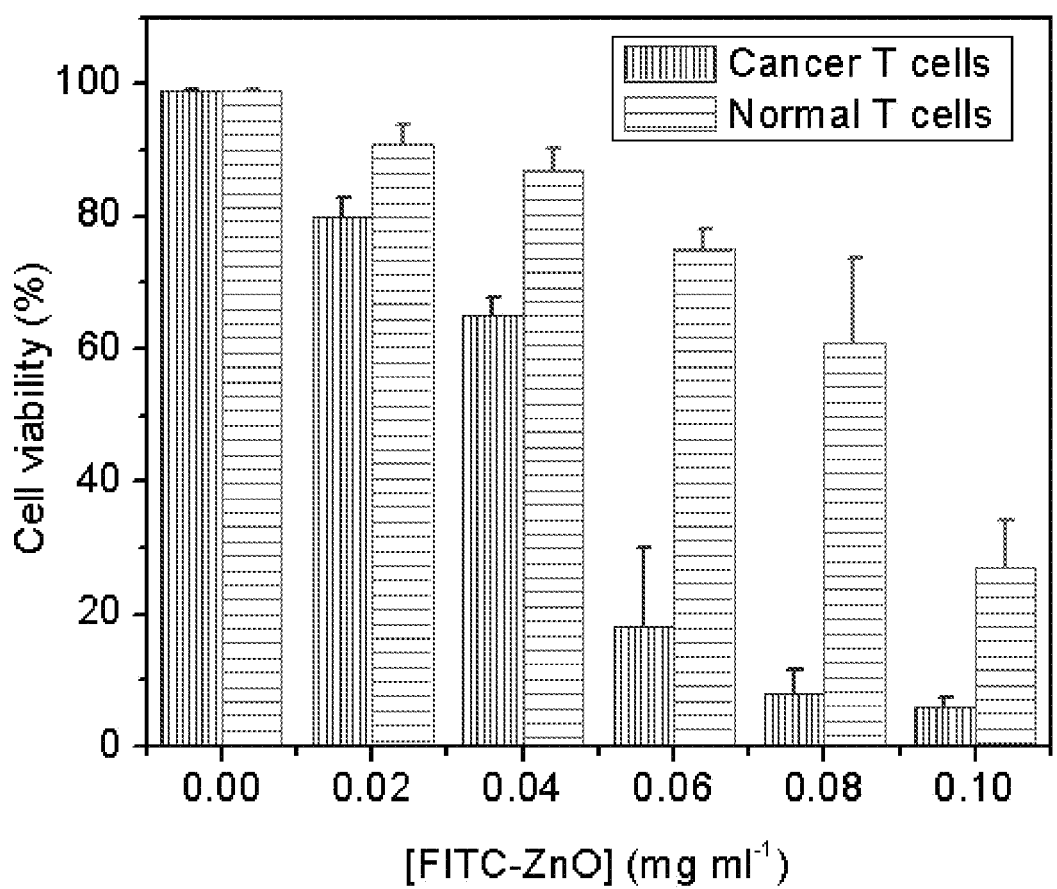
FIG. 9 is a chart about concentration-dependent cytotoxicity of FITC-ZnO particles for leukemia T cells and normal human T cells.

Flow cytometry was used to determine the number of viable human cancerous T cells compared to normal primary T cells after exposure to FITC/SiO$_2$—ZnO particles for 24 h. FIG. 9 shows that FITC/SiO$_2$—ZnO particles reduced cell viability of Jurkat T leukemia cells to 8% at concentrations $\geqq$80 µg/mL, whereas the viability of normal CD4$^+$ T cells at this concentration remained at ~61%. Importantly, the differential toxicity of FITC/SiO$_2$—ZnO particles to cancerous and normal body cells is similar to observations in our lab involving unlabeled ZnO nanoparticles and indicates a potential new utility of ZnO nanoparticles in the treatment of human cancers.

Therefore, the present invention is well adapted to attain the ends and advantages mentioned as well as those that are inherent therein. The particular embodiments disclosed above are illustrative only, as the present invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope and spirit of the present invention. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the element that it introduces. If there is any conflict in the usages of a word or term in this specification and one or more patent or other documents that may be incorporated herein by reference, the definitions that are consistent with this specification should be adopted.

What is claimed is:

1. A core-shell nanoparticle comprising:
a core comprising a fluorophore and a first oxide of a first metal, and
a first shell comprising a second oxide of a second metal wherein the first oxide and the second oxide are different.

2. The core-shell nanoparticle of claim 1, wherein the core-shell nanoparticle comprises at least a second shell that comprises a third oxide of a third metal, and the core-shell nanoparticle has an onion configuration.

3. The core-shell nanoparticle of claim 1, wherein the fluorophore is at least one fluorophore selected from the group consisting of a coumarin dye including hydroxycoumarin, methoxycoumarin, aminocoumarin; a sulfonated; a cyanine dye including Cy3 and Cy5; a fluorescein dye including fluorescein isothiocyanate; a rhodamine dye including tetramethyltrhodmine-5-(and 6)-isothiocyanate; a magnesium dye; a metal ligand complex; derivatives thereof; and combinations thereof.

4. The core-shell nanoparticle of claim 1, wherein the first oxide comprises a material selected from the group consisting of an oxide of magnesium, calcium, strontium, barium, scandium, titanium, vanadium, chromium, manganese, iron, cobalt, nickel, copper, zinc, molybdenum, ruthenium, palladium, silver, cadmium, tungsten, neodymium, gadolinium, erbium, aluminum, silicon, gallium, germanium, indium, tin, lead, all oxidation states thereof, and any combination thereof.

5. The core-shell nanoparticle of claim 1, wherein the second oxide comprises a material selected from the group consisting of an oxide of magnesium, calcium, strontium, barium, scandium, titanium, vanadium, chromium, manganese, iron, cobalt, nickel, copper, zinc, molybdenum, ruthenium, palladium, silver, cadmium, tungsten, neodymium, gadolinium, erbium, aluminum, silicon, gallium, germanium, indium, tin, lead, all oxidation states thereof, and any combination thereof.

6. The core-shell nanoparticle of claim 1, wherein the core-shell nanoparticle has a diameter of about 0.5 nm to about 500 nm.

7. The core-shell nanoparticle of claim 1, wherein the first shell is about 0.5 nm to about 100 nm thick.

8. The core-shell nanoparticle of claim 1, wherein the core-shell nanoparticle has a shape selected from the group consisting of a sphere, a rod, a wire, a star, a substantially spherical shape, and a substantially spherical shape with facets.

9. The core-shell nanoparticle of claim 1 further comprising a surface coating selected from the group consisting of a surfactant, a polymer, a surfiner, a chemically attached functional group, and combinations thereof.

10. A kit comprising:
a core-shell nanoparticle comprising a core that comprises a fluorophore and a first oxide of a first metal and a shell that comprises a second oxide of a second metal,
wherein the first oxide and the second oxide are different, and
a set of instructions for use.

11. The kit of claim 10, wherein the core-shell nanoparticle is in a wet form or a dry form.

12. The kit of claim 10, wherein the means of administering is selected from the group consisting of intravenous, intraperitoneal, intragastric, oral, intra-tumoral, topical, and combinations thereof.

13. A core-shell nanoparticle comprising:
a core comprising a fluorophore and a first oxide of a first metal;
a first shell having a thickness of about 0.5 nm to about 100 nm and comprising a second oxide of a second metal wherein the first oxide and the second oxide are different;
and wherein the core-shell nanoparticle has a diameter of about 1 nm to about 500 nm.

* * * * *